US008741560B2

(12) United States Patent
Rashtchian et al.

(10) Patent No.: US 8,741,560 B2
(45) Date of Patent: Jun. 3, 2014

(54) STABLE COMPOSITIONS FOR NUCLEIC ACID AMPLIFICATION AND SEQUENCING

(75) Inventors: Ayoub Rashtchian, Gaithersburg, MD (US); Joseph Solus, Gaithersburg, MD (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/345,632

(22) Filed: Jan. 6, 2012

(65) Prior Publication Data

US 2012/0142007 A1    Jun. 7, 2012

Related U.S. Application Data

(63) Continuation of application No. 12/129,597, filed on May 29, 2008, which is a continuation of application No. 09/741,664, filed on Dec. 21, 2000, now abandoned, which is a continuation of application No. 09/049,021, filed on Mar. 27, 1998, now abandoned, which is a continuation-in-part of application No. 08/801,720, filed on Feb. 14, 1997, now abandoned, which is a continuation-in-part of application No. 08/689,815, filed on Aug. 14, 1996, now abandoned.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC ..................... 435/6.1; 435/91.2; 536/24.3

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,795,699 A | 1/1989 | Tabor et al. | |
| 4,889,818 A | 12/1989 | Gelfand et al. | |
| 4,962,020 A | 10/1990 | Tabor et al. | |
| 4,965,188 A | 10/1990 | Mullis et al. | |
| 5,173,411 A | 12/1992 | Tabor et al. | |
| 5,338,671 A * | 8/1994 | Scalice et al. | 435/91.2 |
| 5,374,553 A | 12/1994 | Gelfand et al. | |
| 5,409,818 A | 4/1995 | Davey et al. | |
| 5,411,876 A | 5/1995 | Bloch et al. | |
| 5,420,029 A | 5/1995 | Gelfand et al. | |
| 5,436,149 A | 7/1995 | Barnes | |
| 5,455,166 A | 10/1995 | Walker | |
| 5,466,591 A | 11/1995 | Abramson et al. | |
| 5,489,523 A | 2/1996 | Mathur | |
| 5,498,523 A | 3/1996 | Tabor et al. | |
| 5,512,462 A | 4/1996 | Cheng | |
| 5,543,296 A * | 8/1996 | Sobol et al. | 435/6.16 |
| 5,556,772 A | 9/1996 | Sorge et al. | |
| 5,587,287 A | 12/1996 | Scalice et al. | |
| 5,618,703 A * | 4/1997 | Gelfand et al. | 435/91.2 |
| 5,618,711 A | 4/1997 | Gelfand et al. | |
| 5,624,833 A | 4/1997 | Gelfand et al. | |
| 5,652,225 A | 7/1997 | Isner | |
| 5,795,762 A | 8/1998 | Abramson et al. | |
| 5,814,502 A * | 9/1998 | Hoeltke et al. | 435/188 |
| 6,346,379 B1 | 2/2002 | Gelfand et al. | |
| 7,638,612 B2 | 12/2009 | Rashtchian et al. | |
| 2001/0041334 A1 | 11/2001 | Rashtchian et al. | |
| 2009/0233283 A1 | 9/2009 | Rashtchian et al. | |
| 2012/0142007 A1 | 6/2012 | Rashtchian et al. | |

FOREIGN PATENT DOCUMENTS

| | | | |
|---|---|---|---|
| EP | 0329822 B1 | 8/1989 | |
| EP | 0534858 A1 | 3/1993 | |
| EP | 0648280 | 4/1995 | |
| EP | 0776970 A1 | 6/1997 | |
| EP | 0854196 A1 | 7/1998 | |
| EP | 0684315 B1 | 6/2002 | |
| EP | 2264045 | 12/2010 | |
| WO | WO-89/06691 A2 | 7/1989 | |
| WO | WO-90/08839 A1 | 8/1990 | |
| WO | WO-92/06188 | 4/1992 | |
| WO | WO-92/06200 | 4/1992 | |
| WO | WO-92/09689 A1 | 6/1992 | |
| WO | WO-94/26766 A1 | 11/1994 | |
| WO | WO 95/00664 * | 1/1995 | 435/6 |
| WO | WO-95/00664 A1 | 1/1995 | |
| WO | WO-95/16028 A1 | 6/1995 | |
| WO | WO-96/10640 | 4/1996 | |
| WO | WO-97/37038 A1 | 10/1997 | |
| WO | WO-98/06736 | 2/1998 | |

OTHER PUBLICATIONS

Barnes (PNAS, vol. 91, pp. 2216-2220, 1994).*
Barnes, Wayne M. , "PCR amplification of up to 35-kb DNA with high fidelity and high yield from Lamda bacteriophage templates", *Proceedings of the National Academy of Sciences, Genetics*, vol. 91, The National Academy of Sciences of the United States of America, Mar. 1994, 2216-2220.
Bej, Asim K. et al., "Thermostable DNA Polymerases for in Vitro DNA Amplifications", *PCR Technology Current Innovations*, Chapter 25, CRC Press,, 1994, 219-237.

(Continued)

Primary Examiner — Jehanne Sitton

(57) ABSTRACT

The present invention is directed to compositions comprising mixtures of reagents, including thermostable enzymes (e.g., thermostable DNA polymerases), buffers, cofactors and other components, suitable for immediate use in nucleic acid amplification or sequencing techniques without dilution or addition of further components. The compositions contain no stabilizing agents (e.g., glycerol or serum albumin) and unexpectedly maintain activity for extended periods of time upon storage at temperatures above freezing. These compositions are useful, alone or in the form of kits, for nucleic acid amplification (e.g., by the Polymerase Chain Reaction) and sequencing (e.g., by dideoxy or "Sanger" sequencing), or for any procedure utilizing thermostable DNA polymerases in a variety of medical, forensic and agricultural applications. In particular, the compositions and methods are useful for amplifying and sequencing nucleic acid molecules that are larger than about 7 kilobases in size.

25 Claims, 2 Drawing Sheets

(56) References Cited

OTHER PUBLICATIONS

Caetano-Anolles, Gustavo et al., "DNA Amplification Fingerprinting Using Very Short Arbitrary Oligonucleotides", *Bio/Technology*, vol. 9, No. 6, Jun. 1, 1991, 553-557.

Chang, et al., "Development of an ELISA for myeloperoxidase on microplate: Normal reference values and effect of temperature on specimen preparation", *Clinica Chimica Acta*, vol. 373, Issues 1-2,, Nov. 2006, 158-163.

Chou, Quin et al., "Prevention of pre-PCR mis-priming and primer dimerization improves low-copy-number amplifications", *Nucleic Acids Research*, vol. 20, No. 7, Oxford University Press, 1992, 1717-1723.

Daiss, John L. et al., "Topographical characterization of the DNA polymerase from Thermus aquaticus Defining groups of inhibitor mAbs by epitope mapping and functional analysis using surface plasmon resonance", *Journal of Immunological Methods, Uses of Biosensors in Immunology*, vol. 183, Issue 1,, Jun. 14, 1995, 15-26.

D'Aquila, Richard T. et al., "Maximizing sensitivity and specificity of PCR by pre-amplification heating", *Nucleic Acids Research*, vol. 19, No. 13, Oxford University Press, Jul. 11, 1991, 3749.

EP 10172434.2, "Extended European Search Report", mailed Oct. 13, 2010, 7 pages.

EP 10172434.2, "Response to European Search Report", filed Jun. 14, 2011, 3 pages.

EP 97938279.3, "European Search Report", mailed Dec. 1, 2005, 3 pages.

EP 97938279.3, "Supplementary European Search Report", mailed Jan. 12, 2005, 3 pages.

Fiers, W. et al., "Complete nucleotide sequence of SV40 DNA", *Nature 273, Macmillan Journals Ltd*, vol. 273,, May 11, 1978, 113-120.

Flaman, Jean-Michel et al., "A Rapid PCR Fidelity Assay", *Nucleic Acids Research*, vol. 22, No. 15, Oxford University Press,, Aug. 11, 1994, 3259-3260.

Frohman, Michael A. et al., "Rapid production of full-length cDNAs from rare transcripts: amplification using a single gene-specific oligonucleotide primer,", *Proceedings of the National Academy of Sciences, Biochemistry*, vol. 85,, Dec. 1988, 8998-9002.

Gelfand, David H. et al., "Thermostable DNA Polymerases", *PCR Protocols: A Guide to Methods and Applications*, Chapter 16, Academic Press, Inc.,, 1990, pp. 129-141.

Hammerling, Gunter J. , "Production of Antibody-Producing Hybridomas in the Rodent Systems", *Monoclonal Antibodies and T-Cell Hybridomas: Perspectives and technical advances*, Elsevier/North-Holland Biomedical Press, Amsterdam, The Netherlands,, 1981, 563-681.

Heath, Daniel D. et al., "PCR primed with VNTR core sequences yields species specific patterns and hypervariable probes", *Nucleic Acids Research,*, vol. 21, No. 24, Oxford University Press,, 1993, 5782-5785.

Hibner, Urszula et al., "Fidelity of DNA replication catalysed in vitro on a natural DNA template by the T4 bacteriophage multi-enzyme complex", *Nature*, vol. 285, Macmillan Journals Ltd.,, May 29, 1980, 300-305.

Hinnisdaels, Stefan et al., "Direct cloning of PCR Products Amplified with Pwo DNA Polymerase", *BioTechniques*, vol. 20, No. 2, Eaton Publishing Co.,, Feb. 1, 1996, 187-188.

Huang, H. et al., "Fidelity and Predominant Mutations Produced by Deep Vent Wild-Type and Exonuclease—Deficient DNA Polymearses During In Vitro DNA Amplification", *DNA and Cell Biology*, vol. 15, No. 7,, Jul. 1996, 589-594.

Kaufman, Peter B. et al., "Handbook of Molecular and Cellular Methods in Biology and Medicine", CRC Press, United States of America,, Jul. 15, 1995, 444-469.

Köhler, G. et al., "Continuous cultures of fused cells secreting antibody of predefined specificity", *Nature*, vol. 256,, Aug. 7, 1975, 495-497.

Köhler, G. et al., "Derivation of specific antibody-producing tissue culture and tumor lines by cell fusion", *European Journal of Immunology*, vol. 6, Issue 7, Academic Press Inc.,, Jul. 1976, 511-519.

Köhler, G. et al., "Fusion between immunoglobulin-secreting and nonsecreting myeloma cell lines", *European Journal of Immunology*, vol. 6, Issue 4,, Apr. 1976, 292-295.

Kornberg, Arthur , "Biologic Synthesis of Deoxyribonucleic Acid", *Science*, vol. 131, American Association for the Advancement of Science,, May 20, 1960, 1503-1508.

Kunkel, Thomas A. et al., "On the Fidelity of DNA Replication: The Accuracy of T4 DNA Polymerases in Copying $\phi$X174 DNA In Vitro", *The Journal of Biological Chemistry*, vol. 259, No. 3, American Society of Biological Chemists, Inc,, Feb. 10, 1984, 1539-1545.

Lawyer, Frances C. et al., "High-level Expression, Purification, and Enzymatic characterization of Full-length Thermus aquaticus DNA polymerase and a Truncated Form Deficient in 5' to 3' Exonuclease activity", *PCR Methods and Applications,*, vol. 2, No. 4, Cold Spring Harbor Laboratory Press,, May 1993, 275-287.

Li, Honghua et al., "Direct electrophoretic detection of the allelic state of single DNA molecules in human sperm by using the polymerase chain reation", *Proceedings of the National Academy of Sciences of the United States of America*, vol. 87, National Academy of Sciences,, Jun. 1990, 4580-4584.

Lin, Jhy-Jhu et al., "AFLP(TM): A Novel PCR-Based Assay for Plant and Bacterial DNA Fingerprinting", *Focus,*, vol. 17, No. 2,, 1995, 66-70.

Lundberg, Kelly S. et al., "High-fidelity amplification using a thermostabile DNA polymerase isolated from *Pyrococcus furiosus*", *Gene*, vol. 108, Elsevier Science Publishers B.V.,, 1991, 1-6.

Mattila, P. et al., "Fidelity of DNA synthesis by the *Thermococcus litoralis* DNA polymerase-an extremely heat stable enzyme with proofreading activity", *Nucleic Acids Research*, vol. 19, Issue 18, Sep. 25, 1991, 4967-4973.

Maxam, A. et al., "A new method for sequencing DNA", *Proc. Natl. Acad. Sci. USA*, vol. 74, No. 2,, 1977, pp. 560-564.

Mullis, Kary B. et al., "Specific Synthesis of DNA in Vitro via a Polymerase-Catalyzed Chain Reaction", *Methods in Enzymology*, vol. 155,, 1987, 335-350.

Reddy, V. B. et al., "The Genome of Simian Virus 40", *Science*, vol. 200, No. 4341, American Association for the Advancement of Science,, May 5, 1978, 494-502.

Saiki, Randall K. et al., "Enzymatic Amplification of Beta-Globin Genomic Sequences and Restriction Site Analysis for Diagnosis of Sickle Cell Anemia.", *Science*, vol. 230,, Dec. 20, 1985, 1350-1354.

Saiki, Randall K. et al., "Primer-Directed Enzymatic Amplification of DNA with a Thermostable DNA Polymerase", *Science*, Reports, vol. 239,, Jan. 29, 1988, 487-491.

Sanger, "A Rapid Method for Determining Sequences in DNA by Primed Synthesis with DNA Polymerase", *J. Mol. Biol.*, vol. 94, Issue 3, Academic Press, Inc.,, May 25, 1975, 441-448.

Sanger, F. et al., "DNA sequencing with chain-terminating inhibitors", *Proc. Natl. Acad. Sci. USA*, vol. 74(12), 1977, pp. 5463-5467.

Sanger, F. et al., "Nucleotide Sequence of Bacteriophage Phi X174 DNA", *Nature* Vol. 265, No. 5596,, Feb. 24, 1997, 687-695.

Sharkey, David J. et al., "Antibodies as Thermolabile Switches: high Temperature Triggering for the Polymerase Chain Reaction", *Nature, Bio/Technology*, vol. 12, Nature Publishing Group,, May 1994, 506-509.

Slatko, Barton E. , "Thermal Cycle Dideoxy DNA Sequencing", *Molecular Biotechnology*, vol. 6, Issue 3, Humana Press, Totowa,, Dec. 1996, 311-322.

Sutcliffe, J. G. , "Complete Nucleotide Sequence of the *Escherichia coli* Plasmid pBR332", *Cold Spring Harb. Symp. Quant. Biol. 43*, 1979, 77-90.

Tindall, Kenneth R., "Fidelity of DNA Synthesis by the Thermus aquaticus DNA Polymerase", *Biochemistry*, vol. 27, No. 16, the American Chemical Society,, 1998, 6008-6013.

Vos, Pieter et al., "AFLP: a new technique for DNA fingerprinting", *Nucleic Acids Research*, vol. 23, No. 21, Oxford University Press,, Nov. 11, 1995, 4407-4414.

Welsh, John et al., "Fingerprinting genomes using PCR with arbitrary primers", *Nucleic Acids Research*, Vol. 18, No. 24, Oxford University Press,, Dec. 25, 1990, 7213-7218.

Williams, John G. et al., "DNA polymorphisms amplified by arbitrary primers are useful as genetic markers", *Nucleic Acids Research*, vol. 18, No. 22,, Nov. 25, 1990, 6531-6535.

\* cited by examiner

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 893 amino acids
      (B) TYPE: amino acid
      (C) STRANDEDNESS: single
      (D) TOPOLOGY: linear (xi) SEQUENCE DESCRIPTION: SEQ ID NO: 1:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
                35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
                100                 105                 110

Ala Asp Asp Ile Ile Ala Thr Leu Ala Val Arg Ala Ala Arg Phe Leu
            115                 120                 125

Met Arg Phe Ser Leu Ile Thr Gly Asp Lys Asp Met Leu Gln Leu Val
            130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
```

```
                165                 170                 175
His Gln Ile Pro Asp Leu Leu Ala Leu Thr Gly Asp Ile Asp Asn
            180                 185                 190
Ile Pro Gly Val Thr Gly Ile Gly Glu Lys Thr Ala Val Gln Leu Leu
            195                 200                 205
Gly Lys Tyr Arg Asn Leu Glu Tyr Ile Leu Glu His Ala Arg Glu Leu
            210                 215                 220
Pro Gln Arg Val Arg Lys Ala Leu Leu Arg Asp Arg Glu Val Ala Ile
225                 230                 235                 240
Leu Ser Lys Lys Leu Ala Thr Leu Val Thr Asn Ala Pro Val Glu Val
            245                 250                 255
Asp Trp Glu Glu Met Lys Tyr Arg Gly Tyr Asp Lys Arg Lys Leu Leu
            260                 265                 270
Pro Ile Leu Lys Glu Leu Glu Phe Ala Ser Ile Met Lys Glu Leu Gln
            275                 280                 285
Leu Tyr Glu Glu Ala Glu Pro Thr Gly Tyr Glu Ile Val Lys Asp His
            290                 295                 300
Lys Thr Phe Glu Asp Leu Ile Glu Lys Leu Lys Glu Val Pro Ser Phe
305                 310                 315                 320
Ala Leu Asp Leu Glu Thr Ser Ser Leu Asp Pro Phe Asn Cys Glu Ile
            325                 330                 335
Val Gly Ile Ser Val Ser Phe Lys Pro Lys Thr Ala Tyr Tyr Ile Pro
            340                 345                 350
Leu His His Arg Asn Ala His Asn Leu Asp Glu Thr Leu Val Leu Ser
            355                 360                 365
Lys Leu Lys Glu Ile Leu Glu Asp Pro Ser Ser Lys Ile Val Gly Gln
            370                 375                 380
Asn Leu Lys Tyr Asp Tyr Lys Val Leu Met Val Lys Gly Ile Ser Pro
385                 390                 395                 400
Val Tyr Pro His Phe Asp Thr Met Ile Ala Ala Tyr Leu Leu Glu Pro
            405                 410                 415
Asn Glu Lys Lys Phe Asn Leu Glu Asp Leu Ser Leu Lys Phe Leu Gly
            420                 425                 430
Tyr Lys Met Thr Ser Tyr Gln Glu Leu Met Ser Phe Ser Ser Pro Leu
            435                 440                 445
Phe Gly Phe Ser Phe Ala Asp Val Pro Val Asp Lys Ala Ala Glu Tyr
            450                 455                 460
Ser Cys Glu Asp Ala Asp Ile Thr Tyr Arg Leu Tyr Lys Ile Leu Ser
465                 470                 475                 480
Met Lys Leu His Glu Ala Glu Leu Glu Asn Val Phe Tyr Arg Ile Glu
            485                 490                 495
Met Pro Leu Val Asn Val Leu Ala Arg Met Glu Phe Asn Trp Val Tyr
            500                 505                 510
Val Asp Thr Glu Phe Leu Lys Lys Leu Ser Glu Glu Tyr Gly Lys Lys
            515                 520                 525
Leu Glu Glu Leu Ala Glu Lys Ile Tyr Gln Ile Ala Gly Glu Pro Phe
            530                 535                 540
Asn Ile Asn Ser Pro Lys Gln Val Ser Asn Ile Leu Phe Glu Lys Leu
545                 550                 555                 560
Gly Ile Lys Pro Arg Gly Lys Thr Thr Lys Thr Gly Asp Tyr Ser Thr
            565                 570                 575
Arg Ile Glu Val Leu Glu Glu Ile Ala Asn Glu His Glu Ile Val Pro
            580                 585                 590
```

-continued

```
Leu Ile Leu Glu Phe Arg Lys Ile Leu Lys Leu Lys Ser Thr Tyr Ile
        595                 600                 605

Asp Thr Leu Pro Lys Leu Val Asn Pro Lys Thr Gly Arg Phe His Ala
610                 615                 620

Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asp Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Val Lys Ala Phe Glu Glu Gly Ile Asp Val His Thr Leu
690                 695                 700

Thr Ala Ser Arg Ile Tyr Asn Val Lys Pro Glu Glu Val Asn Glu Glu
705                 710                 715                 720

Met Arg Arg Val Gly Lys Met Val Asn Phe Ser Ile Ile Tyr Gly Val
                725                 730                 735

Thr Pro Tyr Gly Leu Ser Val Arg Leu Gly Ile Pro Val Lys Glu Ala
            740                 745                 750

Glu Lys Met Ile Ile Ser Tyr Phe Thr Leu Tyr Pro Lys Val Arg Ser
        755                 760                 765

Tyr Ile Gln Gln Val Val Ala Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Lys Asn Thr Gln Ser Glu Gly Glu Arg Ile Ala Ile Asn Thr Pro Ile
                805                 810                 815

Gln Gly Thr Ala Ala Asp Ile Ile Lys Leu Ala Met Ile Asp Ile Asp
            820                 825                 830

Glu Glu Leu Arg Lys Arg Asn Met Lys Ser Arg Met Ile Ile Gln Val
        835                 840                 845

His Asp Glu Leu Val Phe Glu Val Pro Asp Glu Glu Lys Glu Glu Leu
850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
                885                 890

(2) INFORMATION FOR SEQ ID NO: 2:

(i) SEQUENCE CHARACTERISTICS:
        (A) LENGTH: 893 amino acids
        (B) TYPE: amino acid
        (C) STRANDEDNESS: single
        (D) TOPOLOGY: linear (xi) SEQUENCE DESCRIPTION: SEQ ID NO: 2:

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60
```

```
Ala Ala Thr Phe Arg His Lys Leu Leu Val Ser Asp Lys Ala Gln Arg
 65                  70                  75                  80

Pro Lys Thr Pro Ala Leu Leu Val Gln Gln Leu Pro Tyr Ile Lys Arg
                 85                  90                  95

Leu Ile Glu Ala Leu Gly Phe Lys Val Leu Glu Leu Glu Gly Tyr Glu
            100                 105                 110

Ala Asp Asp Ile Ile Ala Thr Leu Ala Val Arg Ala Ala Arg Phe Leu
            115                 120                 125

Met Arg Phe Ser Leu Ile Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Asp Ile Asp Asn
            180                 185                 190

Ile Pro Gly Val Thr Gly Ile Gly Glu Lys Thr Ala Val Gln Leu Leu
            195                 200                 205

Gly Lys Tyr Arg Asn Leu Glu Tyr Ile Leu Glu His Ala Arg Glu Leu
    210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
    275                 280                 285

Leu Tyr Glu Glu Ala Glu Pro Thr Gly Tyr Glu Ile Val Lys Asp His
    290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
                325                 330                 335

Val Gly Ile Ser Val Ser Phe Lys Pro Lys Thr Ala Tyr Tyr Ile Pro
            340                 345                 350

Leu His His Arg Asn Ala His Asn Leu Asp Glu Thr Leu Val Leu Ser
            355                 360                 365

Lys Leu Lys Glu Ile Leu Glu Asp Pro Ser Ser Lys Ile Val Gly Gln
    370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                405                 410                 415

Asn Glu Lys Lys Phe Asn Leu Glu Asp Leu Ser Leu Lys Phe Leu Gly
            420                 425                 430

Tyr Lys Met Thr Ser Tyr Gln Glu Leu Met Ser Phe Ser Ser Pro Leu
    435                 440                 445

Phe Gly Phe Ser Phe Ala Asp Val Pro Val Asp Lys Ala Ala Glu Tyr
    450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
                485                 490                 495
```

-continued

```
Met Pro Leu Val Asn Val Leu Ala Arg Met Glu Phe Asn Trp Val Tyr
            500                 505                 510
Val Asp Thr Glu Phe Leu Lys Lys Leu Ser Glu Glu Tyr Gly Lys Lys
            515                 520                 525
Leu Glu Glu Leu Ala Glu Lys Ile Tyr Gln Ile Ala Gly Glu Pro Phe
530                 535                 540
Asn Ile Asn Ser Pro Lys Gln Val Ser Asn Ile Leu Phe Glu Lys Leu
545                 550                 555                 560
Gly Ile Lys Pro Arg Gly Lys Thr Thr Lys Thr Gly Asp Tyr Ser Thr
            565                 570                 575
Arg Ile Glu Val Leu Glu Glu Ile Ala Asn Glu His Glu Ile Val Pro
            580                 585                 590
Leu Ile Leu Glu Phe Arg Lys Ile Leu Lys Leu Lys Ser Thr Tyr Ile
            595                 600                 605
Asp Thr Leu Pro Lys Leu Val Asn Pro Lys Thr Gly Arg Phe His Ala
            610                 615                 620
Ser Phe His Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
            645                 650                 655
Arg Lys Ala Ile Val Pro Gln Asp Pro Asp Trp Trp Ile Val Ser Ala
            660                 665                 670
Asp Tyr Ser Gln Ile Glu Leu Arg Ile Leu Ala His Leu Ser Gly Asp
            675                 680                 685
Glu Asn Leu Val Lys Ala Phe Glu Glu Gly Ile Asp Val His Thr Leu
690                 695                 700
Thr Ala Ser Arg Ile Tyr Asn Val Lys Pro Glu Glu Val Asn Glu Glu
705                 710                 715                 720
Met Arg Arg Val Gly Lys Met Val Asn Tyr Ser Ile Ile Tyr Gly Val
            725                 730                 735
Thr Pro Tyr Gly Leu Ser Val Arg Leu Gly Ile Pro Val Lys Glu Ala
            740                 745                 750
Glu Lys Met Ile Ile Ser Tyr Phe Thr Leu Tyr Pro Lys Val Arg Ser
            755                 760                 765
Tyr Ile Gln Gln Val Val Ala Glu Ala Lys Glu Lys Gly Tyr Val Arg
            770                 775                 780
Thr Leu Phe Gly Arg Lys Arg Asp Ile Pro Gln Leu Met Ala Arg Asp
785                 790                 795                 800
Lys Asn Thr Gln Ser Glu Gly Glu Arg Ile Ala Ile Asn Thr Pro Ile
            805                 810                 815
Gln Gly Thr Ala Ala Asp Ile Ile Lys Leu Ala Met Ile Asp Ile Asp
            820                 825                 830
Glu Glu Leu Arg Lys Arg Asn Met Lys Ser Arg Met Ile Ile Gln Val
            835                 840                 845
His Asp Glu Leu Val Phe Glu Val Pro Asp Glu Glu Lys Glu Glu Leu
            850                 855                 860
Val Asp Leu Val Lys Asn Lys Met Thr Asn Val Val Lys Leu Ser Val
865                 870                 875                 880
Pro Leu Glu Val Asp Ile Ser Ile Gly Lys Ser Trp Ser
            885                 890
```

STABLE COMPOSITIONS FOR NUCLEIC ACID AMPLIFICATION AND SEQUENCING

CROSS REFERENCE TO RELATED APPLICATIONS

This application is a continuation of U.S. application Ser. No. 12/129,597, filed May 29, 2008 (pending); which is a continuation of U.S. application Ser. No. 09/741,664, filed Dec. 21, 2000 (now abandoned); which is a continuation of U.S. application Ser. No. 09/049,021, filed Mar. 27, 1998 (now abandoned); which is a continuation-in-part of U.S. application Ser. No. 08/801,720, filed Feb. 14, 1997 (now abandoned); which is a continuation-in-part of U.S. application Ser. No. 08/689,815, filed Aug. 14, 1996 (now abandoned), the contents of all of which are fully incorporated herein by reference in their entireties.

FIELD OF THE INVENTION

This invention is in the fields of molecular and cellular biology. The invention is particularly directed to reagent compositions for use in techniques whereby nucleic acids (DNA or RNA) are amplified or sequenced, and to methods of amplifying and sequencing long nucleic acid molecules, especially via the polymerase chain reaction (PCR).

BACKGROUND OF THE INVENTION

DNA Polymerases

During growth and reproduction of viruses and cellular organisms, the DNA containing the parental genetic information must be faithfully copied and passed on to the progeny. This highly regulated process of DNA replication is carried out in vivo by a complex of enzymes and associated proteins and cofactors (Kornberg, A., *Science* 131:1503-1508, 1959; Hibner, U., and Alberts, B. M., *Nature* 285:300-305, 1980). The primary enzymes taking part in this process are the DNA polymerases, which catalyze the addition of deoxynucleoside triphosphate (dNTP) bases into the newly forming DNA strands. Together with other enzymes (e.g., helicases, ligases and ATPases), the DNA polymerases thus ensure rapid and relatively faithful replication of DNA in preparation for proliferation in prokaryotes, eukaryotes and viruses.

DNA polymerases are also used to manipulate DNA in vitro in a variety of molecular genetic techniques. These enzymes have proven useful not only for in vitro DNA synthesis, but also for determining the nucleotide sequence (i.e., "sequencing") of DNA fragments or genes. This latter application relies on the fact that, in addition to an activity which adds dNTPs to DNA in the 5' to 3' direction (i.e., "polymerase" activity), many DNA polymerases also possess activities which remove dNTPs in the 5' to 3' and/or the 3' to 5' direction (i.e., "exonuclease" activity). DNA polymerases can also be used for sequencing via their incorporation of labeled chain-terminating agents such as dideoxynucleoside triphosphates (See U.S. Pat. Nos. 4,962,020; 5,173,411; and 5,498,523). Thus the same enzyme, e.g., DNA polymerases I and III from the bacterium *Escherichia coli*, DNA polymerase γ from animal cells or DNA polymerase from bacteriophage T7 (See U.S. Pat. No. 4,795,699), may be used in vitro both for DNA synthesis, involving the elongation of the DNA strand, and for DNA sequencing, involving either the synthesis or the digestion of the DNA strand.

The dual activity of certain DNA polymerases is, however, a drawback for some in vitro applications. For example, the in vitro synthesis of an intact copy of a DNA fragment by the polymerase activity, an elongation process which proceeds in a 5' to 3' direction along the template DNA strand, is jeopardized by the exonuclease activities which may simultaneously or subsequently degrade the newly formed DNA. To overcome this technical problem, a fragment of *E. coli* DNA polymerase I lacking the 5' to 3' exonuclease activity (named the "Klenow fragment" after its discoverer) is often employed for in vitro DNA synthesis. The Klenow fragment provides for in vitro DNA synthesis at approximately the same rate as intact *E. coli* DNA polymerase I, but the newly synthesized DNA molecules are less subject to enzymatic degradation and are correspondingly more stable.

Unfortunately, the error rate (i.e., the rate at which incorrect dNTPs are incorporated into the new DNA strand by the enzyme) is somewhat higher for the Klenow fragment than for many other commonly used DNA polymerases, including *E. coli* DNA polymerases I and II and the polymerases from bacteriophages T4 and T7 (Kunkel, T. A., et al., *J. Biol. Chem.* 259:1539-1545, 1984; Tindall, K. R., and Kunkel, T. A., *Biochemistry* 27:6008-6013, 1988; Mattila, P., et al., *Nucl. Acids Res.* 19:4967-4973, 1991). Thus, until recently the rates of synthesis, degradation and error had to be weighed together when choosing which DNA polymerase to use for in vitro DNA synthesis.

DNA Sequencing

In general, two techniques have been traditionally used to sequence nucleic acids. In the first method, termed "Maxam and Gilbert sequencing" after its co-developers (Maxam, A. M. and Gilbert, W., *Proc. Natl. Acad. Sci. USA* 74:560-564, 1977), DNA is radiolabeled, divided into four samples and treated with chemicals that selectively destroy specific nucleotide bases in the DNA and cleave the molecule at the sites of damage. By separating the resultant fragments into discrete bands by gel electrophoresis and exposing the gel to X-ray film, the sequence of the original DNA molecule can be read from the film. This technique has been used to determine the sequences of certain complex DNA molecules, including the primate virus SV40 (Fiers, W., et al., *Nature* 273:113-120, 1978; Reddy, V. B., et al., *Science* 200:494-502, 1978) and the bacterial plasmid pBR322 (Sutcliffe, G., *Cold Spring Harbor Symp. Quant. Biol.* 43:77-90, 1979).

An alternative technique for sequencing, named "Sanger sequencing" after its developer (Sanger, F., and Coulson, A. R., *J. Mol. Biol.* 94:444-448, 1975), is more commonly employed. This method uses the DNA-synthesizing activity of DNA polymerases which, when combined with mixtures of reaction-terminating dideoxynucleoside triphosphates (Sanger, F., et al., *Proc. Natl. Acad. Sci. USA* 74:5463-5467, 1977) and a short primer (either of which may be detectably labeled), gives rise to a series of newly synthesized DNA fragments specifically terminated at one of the four dideoxy bases. These fragments are then resolved by gel electrophoresis and the sequence determined as described for Maxam and Gilbert sequencing above. By carrying out four separate reactions (once with each ddNTP), the sequences of even fairly complex DNA molecules may rapidly be determined (Sanger, F., et al., *Nature* 265:678-695, 1977; Barnes, W., *Meth. Enzymol.* 152:538-556, 1987). While Sanger sequencing usually employs *E. coli* or T7 DNA polymerase (U.S. Pat. No. 4,795, 699), recent modifications of this technique using T7 polymerase mutants allow sequencing to be accomplished using a single sequencing reaction containing all four chain-terminating ddNTPs at different concentrations (U.S. Pat. Nos. 4,962,020 and 5,173,411). Further modifications to the technique, to reduce or eliminate the buildup of reaction-poisoning pyrophosphate in the reaction mixtures, have also been described (U.S. Pat. No. 5,498,523).

The Polymerase Chain Reaction

Soon after their identification and characterization, it was recognized that the activities of the various enzymes and cofactors involved in DNA synthesis could be exploited in vitro to dramatically increase the concentration of, or "amplify," one or more selected DNA sequences. For many medical, diagnostic and forensic applications, amplification of a particular DNA sequence is essential to allow its detection in, or isolation from, a sample in which it is present in very low amounts. More recently, in vitro amplification of specific genes has provided powerful and less costly means to facilitate the production of therapeutic proteins by molecular biological techniques, and may have applications in genetic therapy as well.

While a variety of nucleic acid amplification processes has been described, the most commonly employed is the Polymerase Chain Reaction (PCR) technique disclosed in U.S. Pat. Nos. 4,683,195 and 4,683,202. In this process, a sample containing the nucleic acid sequence to be amplified (the "target sequence") is first heated to denature or separate the two strands of the nucleic acid. The sample is then cooled and mixed with specific oligonucleotide primers which hybridize to the target sequence. Following this hybridization, DNA polymerase in a buffered aqueous solution is added to the sample, along with a mixture of the dNTPs that are linked by the polymerase to the replicating nucleic acid strand. After allowing polymerization to proceed to completion, the products are again heat-denatured, subjected to another round of primer hybridization and polymerase replication, and this process repeated any number of times. Since each nucleic acid product of a given cycle of this process serves as a template for production of two new nucleic acid molecules (one from each parent strand), the PCR process results in an exponential increase in the concentration of the target sequence. Thus, in a well-controlled, high-fidelity PCR process, as few as 20 cycles can result in an over one million-fold amplification of the target nucleic acid sequence (See U.S. Pat. Nos. 4,683,195 and 4,683,202).

Thermostable DNA Polymerases

Overview

Initially, the DNA polymerases of choice for use in DNA sequencing or PCR were *E. coli* DNA polymerase I, the Klenow fragment, or T4 or T7 polymerases owing to their ease of isolation and well-characterized activities. However, the use of these enzymes necessitated their addition prior to the start of each sequencing or PCR cycle, due to their thermolability at the temperatures used to denature the DNA strands in the initial steps of the processes (typically 70° to 95° C.) (Saiki, R. K., et al., *Science* 230:1350-1354, 1985; Mullis, K. B., and Faloona, F. A., *Meth. Enzymol.* 155:335-350, 1987; U.S. Pat. No. 4,795,699). This need for the addition of fresh enzyme at the beginning of each cycle increased the amount of time required for these processes, and increased the risk of operator error and contamination of the samples during reagent introduction, often leading to undesirable results.

These difficulties were partially overcome by the use of thermo stable DNA polymerases in the PCR process (Saiki, R. K., et al., *Science* 239:487-491, 1988). The thermostable DNA polymerase most commonly used in PCR is Taq polymerase, isolated from the thermophilic bacterium *Thermus aquaticus* (Saiki et al., 1988, Id; U.S. Pat. Nos. 4,889,818 and 4,965,188). Taq polymerase functions optimally at temperatures of 70-80° C., and is able to maintain substantial activity upon repeated exposure to temperatures of 92°-95° C. as are often used in the initial steps of PCR (Gelfand, D. H., and White, T. J., in: *PCR Protocols: A Guide to Methods and Applications*, Innis, M. A., et al., eds., Academic Press, pp. 129-141, 1989; Bej, A. K., and Mahbubani, M. H., in: *PCR Technology: Current Innovations*, Griffin, H. G., and Griffin, A. M., eds., CRC Press, pp. 219-237, 1994).

The use of Taq polymerase in PCR eliminated the need to add fresh enzyme to the reaction mix prior to each PCR cycle. Instead, a quantity of Taq polymerase sufficient to catalyze DNA polymerization over the desired number of cycles can be mixed with the other components prior to the initiation of the first PCR cycle, and the enzyme continues to function throughout the repetitive cycles of increased and decreased temperatures. The use of Taq polymerase has also facilitated the automation of the PCR process (Gelfand and White, Id), thereby at once dramatically reducing time constraints and the risks of operator error and sample contamination that are problematic with thermolabile polymerases. Currently, most PCR amplification of nucleic acids for industrial and academic applications is performed using Taq polymerase and automated thermal cycling instrumentation.

In addition to Taq polymerase, other thermostable polymerases have found similar application in PCR (Bej and Mahbubani, Id). Particularly useful as substitutes for Taq polymerase in PCR are polymerases isolated from the thermophilic bacteria *Thermus thermophilus* (Tth polymerase), *Thermococcus litoralis* (Tli or VENT™ polymerase), *Pyrococcus furiosus* (Pfu or DEEPVENT polymerase), *Pyrococcus woosii* (Pwo polymerase) and other *Pyrococcus* species, *Bacillus sterothermophilus* (Bst polymerase), *Sulfolobus acidocaldarius* (Sac polymerase), *Thermoplasma acidophilum* (Tac polymerase), *Thermus flavus* (Tfl/Tub polymerase), *Thermus ruber* (Tru polymerase), *Thermus brockianus* (DYNAZYME™ polymerase), *Thermotoga neapolitana* (Tne polymerase; See WO 96/10640), *Thermotoga maritima* (Tma polymerase; See U.S. Pat. No. 5,374,553) and other species of the *Thermotoga* genus (Tsp polymerase) and *Methanobacterium thermoautotrophicum* (Mth polymerase). While each of these polymerases is useful for particular applications (See Bej and Mahbubani, Id., p. 222), Taq polymerase is still by far the most commonly used polymerase in PCR.

Thermostable polymerases have also found application in DNA sequencing techniques, particularly in automated methods of dideoxy sequencing such as "cycle sequencing." These approaches resemble PCR in most respects except that, in place of dNTPs, automated DNA sequencing uses ddNTPs which allow determination of the sequence of the template DNA as described above. Use of higher denaturation temperatures in automated sequencing also improves sequencing efficiency (i.e., fewer misincorporations occur) and allows the sequencing of templates that are GC-rich or contain significant secondary structure (such as supercoiling).

The use of thermolabile DNA polymerases such as *E. coli* or T7 DNA polymerases in these approaches, however, is subject to the same limitations described above for their use in PCR. Accordingly, automated methods of DNA sequencing utilizing higher temperatures have increasingly employed thermostable DNA polymerases, the most commonly used of which is, as for PCR, Taq polymerase.

Technical Limitations

The use of Taq and other thermostable polymerases in sequencing and PCR is not, however, without drawback. For example, the error rate for Taq polymerase is substantially higher (i.e., the final product is of "lower fidelity") than that for most of the thermolabile DNA polymerases, including the Klenow fragment of *E. coli* DNA polymerase I (Tindall and Kunkel, Id.), averaging about $10^{-4}$ misincorporations per base pair per cycle. In addition, Taq polymerase is only useful for amplifying relatively short stretches of DNA (maximum length on the order of 5-6 kilobases; Barnes, W. M., *Proc. Natl. Acad Sci. USA* 91:2216-2220, 1994), thus precluding its use in PCR amplification of large genes and whole genomes as is necessary in many current applications.

These technical limitations are apparently related: it has been theorized that the Taq polymerase PCR length limitation is due to the low efficiency of elongation of the newly synthesized DNA strands at the sites of incorporation of mismatched bases in the parent strands (Barnes, Id). Further contributing to this difficulty is the absence in Taq polymerase of a 3' to 5' exonuclease activity, which in other polymerases acts in a "proofreading" capacity to correct these mismatches and reduce the error rate (Bej and Mahbubani, Id). The 5' to 3' exonuclease activity present in most thermostable DNA polymerases can also degrade the 5' ends of the oligonucleotide primers (also a complication with the 3' to 5' exonuclease activity which can degrade the 3' ends of the primers), yielding undesirable results due to an early termination of the PCR process (See WO 92/06200; Barnes, Id).

In sequencing reactions, Taq polymerase is subject to a limitation shared by *E. coli* polymerase I and the Klenow fragment. These enzymes each are "discriminatory," meaning that they preferentially incorporate dNTPs over ddNTPs into newly synthesized DNA. Thus, to use Taq polymerase in automated sequencing reactions, relatively high concentrations of ddNTPs must be maintained in the reaction mixtures, to kinetically favor ddNTP incorporation by the enzyme. This need for high levels of ddNTPs can be prohibitively expensive, particularly when large DNA fragments are being sequenced.

As another technical limitation, the DNA polymerases have heretofore been maintained in highly concentrated stock solutions in storage buffers containing glycerol, bovine serum albumin and/or other stabilizing agents and stored at −20° C. or lower (See, e.g., WO 92/06188; U.S. Pat. No. 5,436,149). The conventional understanding in the field has been that the enzymes would rapidly lose activity at more dilute working concentrations (as do many bioactive proteins) and in solutions without glycerol or other stabilizing agents. Moreover, the solutions of enzymes had to be mixed with dNTPs or ddNTPs, cofactors (such as $Mg^{++}$) and one or more detergents immediately prior to use in the sequencing or PCR processes, as it was believed that premixture and storage of these solutions would also deleteriously affect their stability. In addition, dNTPs have traditionally been stored at temperatures below −20° C. and have also been thought to be unstable if stored otherwise (Maniatis, T., et al., *Molecular Cloning, A Laboratory Manual*, CRC Press, 1992). Together, these limitations have made the use of compositions containing thermostable DNA polymerases in DNA sequencing and PCR more costly and time-consuming than would be desired.

Overcoming Technical Limitations

Several approaches have been undertaken to attempt to surmount these technical difficulties. The results of DNA sequencing methodologies, for example, have been improved by the use of mutant Taq enzymes such as ΔTaq (WO 92/06188) lacking the 5' to 3' exonuclease activity. Improved sequencing results have also been obtained by including in the reaction mixture an agent such as pyrophosphatase which breaks down the pyrophosphate that can be formed during dideoxy sequencing reactions (See U.S. Pat. No. 5,498,523). To overcome the discrimination between ddNTPs and dNTPs, some investigators have used T7 DNA polymerase in sequencing, as this enzyme is "nondiscriminatory," meaning that it incorporates ddNTPs at approximately the same rate as dNTPs (See U.S. Pat. No. 4,795,699). Alternatively, mutants of DNA polymerase from a variety of organisms (e.g., *E. coli*) which are nondiscriminatory have also been described; see copending U.S. patent application Ser. No. 08/525,057 of Deb K. Chatterjee, filed Sep. 8, 1995, entitled "Mutant DNA Polymerases and Use Thereof," the disclosure of which is expressly incorporated herein by reference. However, as described above, both *E. coli* and T7 DNA polymerases are thermolabile, so their use in automated sequencing requires addition of fresh enzyme at the beginning of each cycle.

More recently, mutations in Tne polymerase from *Thermotoga neapolitana* have been described, which overcome these limitations (WO 96/10640). One of these mutations, in which a phenylalanine residue at amino acid position number 730 in the wildtype protein (SEQ ID NO:1) is replaced with a tyrosine residue, results in a mutant Tne polymerase (SEQ ID NO:2) which is both thermostable and nondiscriminatory. This mutant Tne polymerase thus provides a solution to both the problems of thermolability and ddNTP discrimination found in other enzymes used in automated DNA sequencing. See also the co-pending U.S. Patent Application of A. John Hughes and Deb K. Chatterjee, entitled "Cloned DNA Polymerases from *Thermotoga* and Mutants Thereof," filed on even day herewith, which is incorporated by reference herein in its entirety.

In PCR applications, the low fidelity of Taq-produced PCR products has been alleviated to some extent by the use of Pfu DNA polymerase which contains the proofreading 3' to 5' exonuclease activity lacking in Taq polymerase (Lundberg, K. S., et al., *Gene* 108:1-6, 1991). Other thermostable DNA polymerases, including Tli/VENT™ (Bej and Mahbubani, Id) and DEEPVENT™ (Flaman, J.-M., et al., *Nucl. Acids Res.* 22(15):3259-3260, 1994) have also been shown to improve the fidelity of PCR products.

As a means of overcoming this length limitation, mutant enzymes lacking the 5' to 3' exonuclease activity have been prepared, including N-terminal deletion mutants of Taq polymerase that are analogous to the Klenow fragment of *E. coli* DNA polymerase I. Several of these mutant enzymes, including Klentaq-1 and Klentaq-278 (Barnes, W. M., *Gene* 112:29-35, 1992; U.S. Pat. No. 5,436,149), the Taq Stoffel fragment (Lawyer, F. C., et al., *PCR Meth. Appl.* 2:275-287, 1993), and mutants of other thermostable DNA polymerases lacking the 5' to 3' exonuclease activity (e.g., those disclosed in WO 92/06200), have been shown to provide increasingly stable PCR products and primers. However, as these enzymes also lack the 3' to 5' proofreading activity, their use subjects the PCR process to the increased error rates described above. Thus, even with these mutant enzymes, high-fidelity PCR amplification of DNA fragments larger than 5-6 kilobases has proven exceedingly difficult.

By combining specific quantities of several enzymes, however, high-fidelity PCR amplification of large DNA sequences has been achieved. For example, use of a combination of a high concentration of a thermostable DNA polymerase lacking the 3' to 5' exonuclease activity (e.g., Klentaq278) and a low concentration of a thermostable DNA polymerase exhibiting the 3' to 5' exonuclease activity (e.g., Pfu/DEEPVENT or Tli/VENT™) provides for amplification to high concentrations of DNA sequences of at least 35 kilobases in length with significantly improved fidelity (Barnes, Id; U.S. Pat. No. 5,436,149). Similar results have been obtained with mixtures of Tth polymerase and low levels of thermostable polymerases from *Pyrococcus*, Tli or Tma (U.S. Pat. No. 5,512,462). Apparently, the low level of 3' to 5' exonuclease activity is sufficient to remove any mismatched bases incorporated by the majority polymerase, but is insufficient to significantly degrade the primers. While this approach has heretofore been applied to simple DNA sequences such as those from bacteriophage λ, it may prove applicable to larger and more complex sequences as well, including those of the genomes of bacteria, yeast, plants and animals.

Despite its widespread use, however, conventional PCR can produce non-specific amplification fragments which range from small primer-dimer products to target fragments of various yields and of heterogeneous size. These non-specific products not only obscure PCR results, but can also limit the sensitivity of PCR product detection and can also interfere with downstream processes such as DNA sequencing and cloning of PCR fragments. These artifact amplification products are often due to non-specific annealing and extension of primers at low temperatures, and to the presence of a low level of polymerase activity in the reaction mixtures during setup and start of PCR (Li, H., et al., *Proc. Natl. Acad Sci. USA* 87:4580 (1990); Frohman, M. A., et al., *Proc. Natl. Acad Sci. USA* 85:8998 (1988); Chou, Q., et al., *Nucl. Acids Res.* 20:1717 (1992)). Consequently, a number of physical manipulation methods have been developed to circumvent the non-specific priming during the PCR setup and start of the reaction. These manual methods are often referred to as "Hot Start" and involve the addition of Taq DNA polymerase to preheated (typically to about 80° C.) PCR reactions (Chou, Q., et al., *Nucl. Acids Res.* 20:1717 (1992); D'Aquila, R. T., et al. *Nucl. Acids Res.* 19:3749 (1991). These methods, however, are often cumbersome and are not used for routine or high throughput applications.

It has recently been shown that specific monoclonal antibodies to thermostable DNA polymerases can be used to improve specificity of PCR amplification (see U.S. Pat. No. 5,338,671, the disclosure of which is incorporated herein by reference in its entirety; Sharkey, D. J., et al., *BioTechnology* 12:506 (1994); Daiss, J. L. et al., *J. Immunol. Meth.* 183:15 (1995)). These monoclonal antibodies prevent the polymerization activity of the enzyme and result in inactivity of Taq DNA polymerase during the PCR setup and start of reactions. However, during the initial denaturation step of PCR, antibodies are denatured and active Taq DNA polymerase is released into the reaction. This approach provides an effective and automatic method for control of non-specific PCR products in all PCR reactions.

Despite these successes in overcoming the ddNTP discrimination, length, fidelity, and artifact limitations, however, compositions comprising the reagents necessary for DNA sequencing or PCR capable of extended storage above freezing at working concentrations, without stabilizing agents, have not heretofore been reported. Thus, the time and economic constraints to the use of solutions of thermostable enzymes in most applications have yet to be overcome.

BRIEF SUMMARY OF THE INVENTION

The present invention overcomes these temporal and economic limitations of previously available reagent compositions used in nucleic acid amplification and sequencing methods. Specifically, the invention is directed to compositions comprising mixtures of reagents at working concentrations suitable for use with or without dilution and maintaining activity upon storage for an extended time, said mixtures consisting essentially of at least one thermostable enzyme and at least one buffer salt. The invention further provides such compositions for use in nucleic acid amplification further comprising at least one deoxynucleoside triphosphate, magnesium salts and at least one nonionic detergent, wherein the thermostable enzyme is at least one thermostable DNA polymerase. In another embodiment, the invention provides such compositions for use in nucleic acid sequencing further comprising at least one deoxynucleoside triphosphate, at least one dideoxynucleoside triphosphate, magnesium salts and at least one nonionic detergent, wherein the thermostable enzyme is at least one thermostable DNA polymerase. More specifically, the invention is directed to such compositions wherein the thermostable DNA polymerase is Taq, Tne, Tma, Pfu, Pwo or Tth DNA polymerase, or mutants thereof, preferably at concentrations of about 0.1-200 units per milliliter, about 0.1-50 units per milliliter, about 0.1-40 units per milliliter, about 0.1-36 units per milliliter, about 0.1-34 units per milliliter, about 0.1-32 units per milliliter, about 0.1-30 units per milliliter, or about 0.1-20 units per milliliter, and most preferably at concentrations of about 20 units per milliliter. The invention is also directed to such compositions that further comprise VENT or DEEPVENT™ DNA polymerase, preferably at concentrations of about 0.0002-200 units per milliliter, about 0.002-100 units per milliliter, about 0.002-20 units per milliliter, about 0.002-2.0 units per milliliter, about 0.002-1.6 units per milliliter, about 0.002-0.8 units per milliliter, about 0.002-0.4 units per milliliter, or about 0.002-0.2 units per milliliter, most preferably at concentrations of about 0.40 units per milliliter.

In another embodiment, the invention is directed to such compositions which optionally further comprise at least one antibody which specifically binds to the one or more thermostable enzymes (such as the one or more DNA polymerases) in the compositions. The antibodies used in this aspect of the invention may be polyclonal or monoclonal, and are preferably monoclonal, and may include (but are not limited to) anti-DNA polymerase antibodies, particularly antibodies which bind specifically to one or more thermostable DNA polymerases, such as anti-Taq antibodies, anti-Tne antibodies, anti-Tma antibodies, anti-Pfu antibodies, anti-Pwo antibodies, anti-Tth antibodies, and the like. Preferably, the antibodies are used in the compositions at an antibody to polymerase concentration ratio of up to about 100:1, up to about 50:1, up to about 25:1, up to about 20:1, up to about 15:1, up to about 10:1, up to about 9:1, up to about 8:1, up to about 7.5:1, up to about 7:1, up to about 6:1, up to about 5:1, up to about 4:1, up to about 3:1, up to about 2.5:1, up to about 2:1, or up to about 1:1. Most preferably, the antibodies are used in the compositions at an antibody to polymerase concentration ratio of about 1:1 to about 10:1, or about 1:1 to about 5:1.

The invention is further directed to kits for DNA amplification or sequencing, said kits comprising a carrier means, such as a box, carton, tube or the like, having in close confinement therein one or more container means, such as vials, tubes, ampules, bottles or the like, wherein a first container means contains a composition comprising a mixture of reagents at working concentrations suitable for use without dilution and maintaining activity upon storage for extended time, said mixture consisting essentially of at least one thermostable DNA polymerase, buffer salts, magnesium salts and at least one nonionic detergent. In additional embodiments, the kits may optionally comprise one or more antibodies, in the first container means or in a separate container means, which specifically bind to one or more of the DNA polymerases present in the compositions of the kits, such as those antibodies described above. The first container means may also contain a mixture of dNTPs (for PCR applications) or ddNTPs (for sequencing applications). Alternatively, the dNTPs or ddNTPs may be included in a second container means also closely confined within the carrier means of the kit.

The invention is also directed to methods of amplifying or sequencing a nucleic acid molecule, comprising contacting the nucleic acid molecule to be amplified or sequenced, which is preferably larger than about 4-8 kilobases in size, more preferably larger than about 5-7 kilobases in size and most preferably larger than about 7 kilobases in size, with the compositions of the invention. The invention also provides nucleic acid molecules amplified by these methods.

The present invention is also directed more generally to compositions containing thermostable proteins or enzymes useful in molecular biology. These compositions comprise mixtures of reagents at working concentrations suitable for use with or without dilution which maintain the enzyme or protein activity upon storage for an extended time. The compositions of this aspect of the invention comprise at least one thermostable enzyme and at least one buffer salt. The thermostable enzymes in these compositions include, but are not limited to, polymerases, restriction enzymes, alkaline phosphatases, reverse transcriptases, ligases, nucleases, pyrophosphatases, DNAses, RNAses, exonucleases, RNAse inhibitors, kinases, topoisomerases, guanylyltransferases and glycosylases (e.g., uracil DNA glycosylase).

The invention is further directed to kits for conducting a procedure associated with the thermostable enzymes or proteins (restriction enzymes, phosphatases, etc.), the kits comprising a container means such as a box, carton, tube and the like, having in close confinement therein one or more container means, such as a vial, tube, ampule, bottle or the like, wherein a first container means contains a composition comprising a mixture of reagents at working concentrations suitable for use with or without dilution. The reagents in the first container means include at least one thermostable enzyme or protein and at least one buffer salt.

The compositions of the invention have unexpectedly been found to maintain enzyme activity for extended periods of time compared to conventional compositions. For example, the present compositions maintain enzyme activity for at least four weeks when stored at ambient temperature (about 20°-25° C.), for at least one year at about 4° C. and for at least two years at about −20° C.

These stable, ready-to-use reagent compositions are useful for nucleic acid amplification (including the Polymerase Chain Reaction or PCR) and sequencing (including dideoxy sequencing), or for any procedure using thermostable DNA polymerases or other enzymes (restriction enzymes, phosphatases, kinases, etc.) in fields such as medical therapeutics and diagnostics, forensics and agricultural science.

Other features, advantages and applications of the present invention will be apparent to those skilled in the art from the following description of the preferred embodiments thereof, and from the claims.

DETAILED DESCRIPTION OF THE INVENTION

Definitions

Figure 1:
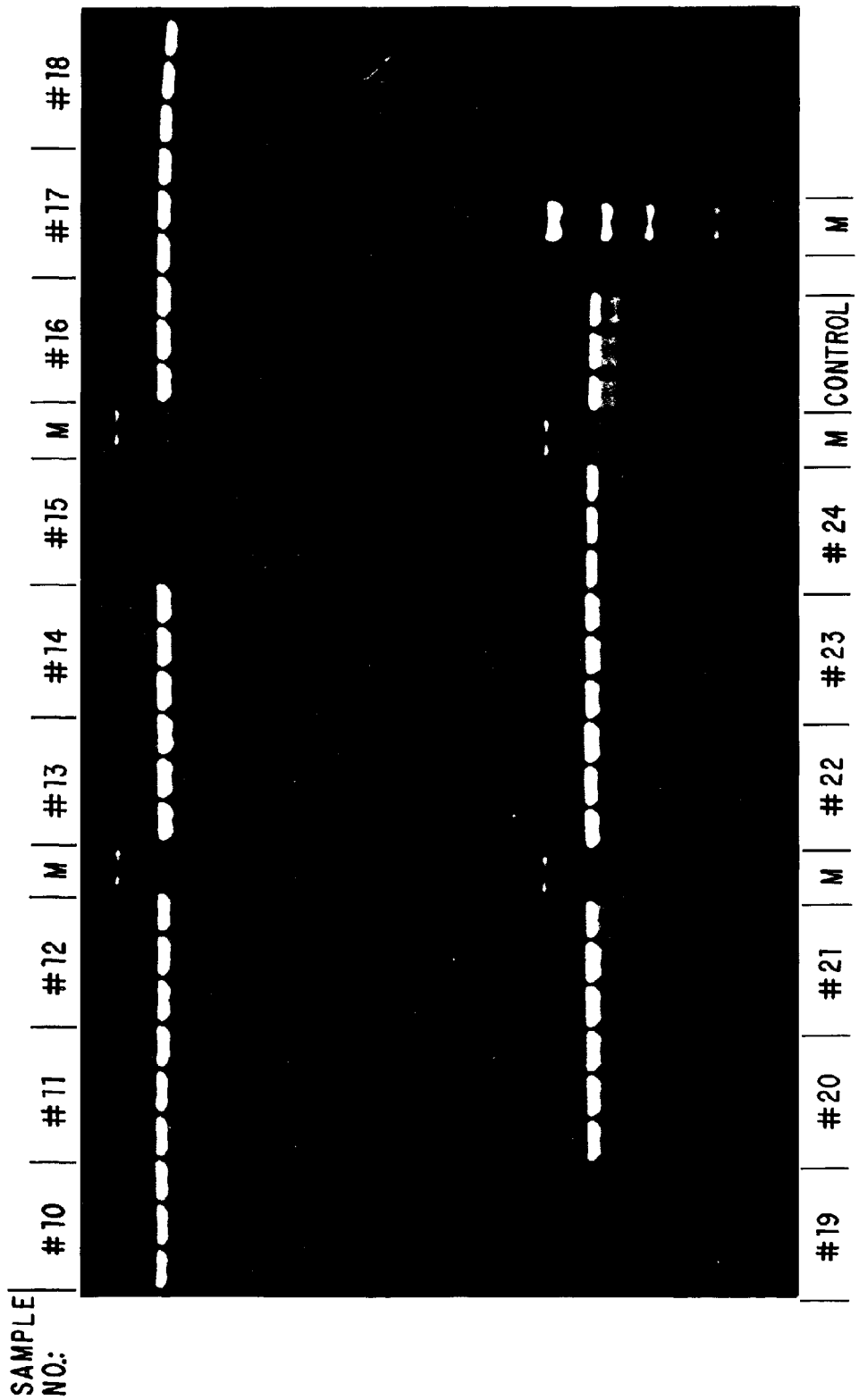
FIG. 1 is a photograph of an agarose gel (visualized by ethidium bromide fluorescence under ultraviolet illumination) of PCR amplification of a 1.3 kilobase human genomic DNA fragment from 10 nanograms of template using 15 different reagent compositions (corresponding to samples 10-24 in Table 1) stored as indicated in Table 1, and a freshly made control sample. Lane marked "M" contains markers indicating amount of DNA loaded; bands correspond to (from top to bottom) 100 nanograms, 60 nanograms, 40 nanograms and 20 nanograms of DNA mass markers.

Throughout this disclosure, various terms that are generally understood by those of routine skill in the art are used. Certain terms as used herein, however, have specific meanings for the purposes of the present invention. The term "dNTP" (plural "dNTPs") generically refers to the deoxynucleoside triphosphates (e.g., dATP, dCTP, dGTP, dTTP, dUTP, dITP, 7-deaza-dGTP, adATP, adTTP, adGTP and adCTP), and the term "ddNTP" (plural "ddNTPs") to their dideoxy counterparts, that are incorporated by polymerase enzymes into newly synthesized nucleic acids. The term "unit" as used herein refers to the activity of an enzyme. When referring to a thermostable DNA polymerase, one unit of activity is the amount of enzyme that will incorporate 10 nanomoles of dNTPs into acid-insoluble material (i.e., DNA or RNA) in 30 minutes under standard primed DNA synthesis conditions. "Working concentration" is used herein to mean the concentration of a reagent that is at or near the optimal concentration used in a solution to perform a particular function (such as amplification, sequencing or digestion of nucleic acids). The term "detergent" as used herein refers to a nonionic surfactant such as TRITON X-100®, Nonidet P-40 (NP-40), Tween 20 or Brij 35. The terms "stable" and "stability" as used herein generally mean the retention by an enzyme of at least 70%, preferably at least 80%, and most preferably at least 90%, of the original enzymatic activity (in units) after the enzyme or composition containing the enzyme has been stored for at least four weeks at a temperature of about 20-25° C., at least one year at a temperature of about 4° C. or at least 2 years at a temperature of −20° C.

Overview

The present invention provides, in a first preferred embodiment, compositions comprising mixtures of at least one thermostable enzyme (e.g., a thermostable DNA polymerase, restriction enzyme, etc.), at least one buffer salt, and other reagents necessary for carrying out the procedure associated with the enzyme(s) (e.g., deoxynucleoside triphosphates (dNTPs) for amplification of nucleic acids, dNTPs and dideoxynucleoside triphosphates (ddNTPs) for sequencing of nucleic acids, etc.). In additional preferred embodiments, the invention provides such compositions which may further comprise one or more antibodies which specifically bind to the one or more thermostable enzymes (such as the one or more DNA polymerases) in the compositions. The compositions of the invention contain no stabilizing compounds (e.g., glycerol, serum albumin or gelatin) that have been traditionally included in stock reagent solutions, and exhibit increased stability (measured as maintenance of enzyme activity) even upon storage at temperatures above freezing. Furthermore, the invention provides these reagent compositions in ready-to-use concentrations, obviating the time-consuming dilution and pre-mixing steps necessary with previously available solutions. Unexpectedly, even at these diluted concentrations the reagent compositions are stable for extended periods of time at temperatures ranging from ambient (about 20-25° C.) to about −70° C.

In additional preferred embodiments, the present invention provides these ready-to-use compositions in the form of kits that are suitable for immediate use to carry out the procedure associated with the enzyme(s) (e.g., nucleic acid amplification or sequencing in the case of DNA polymerases). These kits are also stable for extended periods of time at temperatures ranging from ambient (about 20-25° C.) to −70° C.

In additional preferred embodiments, the invention provides ready-to-use compositions for PCR amplification. The ready-to-use reagents will contain all necessary components for PCR amplification such as one or more DNA polymerase(s), one or more deoxynucleoside triphosphates (dNTPs) and buffers, and optionally one or more other components contributing to efficient amplification of nucleic acid templates by automatic "hot start." Automatic Hot Start PCR can be accomplished by reaction of specific antibodies, e.g., monoclonal antibodies, that bind to and inactivate one or more DNA polymerases, such as thermostable DNA polymerases (e.g., Taq DNA polymerase), that are present in the ready-to-use compositions of the invention. In additional embodiments, the invention provides formulation of ready-to-use PCR reagents which contain one or more thermostable DNA polymerases (e.g., Taq DNA polymerase), one or more dNTPs, one or more buffers, and one or more antibodies that bind to a DNA polymerase.

Sources of Reagents

The compositions of the present invention may be formed by mixing the component reagents at the concentrations described below. The components for making the ready-to-use compositions can be obtained from, for example, Life Technologies, Inc. (Rockville, Md.).

Thermostable Enzymes

The thermostable enzymes (e.g., DNA polymerases, restriction enzymes, phosphatases, etc.) used in the present invention may be isolated from natural or recombinant sources, by techniques that are well-known in the art (See Bej and Mahbubani, Id.; WO 92/06200; WO 96/10640), from a variety of thermophilic bacteria that are available commercially (for example, from American Type Culture Collection, Rockville, Md.) or may be obtained by recombinant DNA techniques (WO 96/10640). Suitable for use as sources of thermostable enzymes or the genes thereof for expression in recombinant systems are the thermophilic bacteria *Thermus thermophilus, Thermococcus litoralis, Pyrococcus furiosus, Pyrococcus woosii* and other species of the *Pyrococcus* genus, *Bacillus sterothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants thereof. It is to be understood, however, that thermostable enzymes from other organisms may also be used in the present invention without departing from the scope or preferred embodiments thereof. As an alternative to isolation, thermostable enzymes (e.g., DNA polymerases) are available commercially from, for example, Life Technologies, Inc. (Rockville, Md.), New England Biolabs (Beverly, Mass.), Finnzymes Oy (Espoo, Finland) and Perkin Elmer Cetus (Norwalk, Conn.). Once obtained, the purified enzymes may be placed into solution at working concentrations and stored according to the methods of the present invention.

dNTPs

The dNTP components of the present compositions serve as the "building blocks" for newly synthesized nucleic acids, being incorporated therein by the action of the polymerases. These dNTPs—deoxyadenosine triphosphate (dATP), deoxycytosine triphosphate (dCTP), deoxyguanosine triphosphate (dGTP), deoxythymidine triphosphate (dTTP), and for some applications deoxyuridine triphosphate (dUTP) and deoxyinosine triphosphate (dITP), α-thio-dATP and 7-deaza-dGTP—are available commercially from sources including Life Technologies, Inc. (Rockville, Md.), New England Biolabs (Beverly, Mass.) and Sigma Chemical Company (Saint Louis, Mo.). The dNTPs may be unlabeled, or they may be detectably labeled by coupling them by methods known in the art with radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin) or other detection agents. Labeled dNTPs may also be obtained commercially, for example from Life Technologies, Inc. (Rockville, Md.) or Sigma Chemical Company (Saint Louis, Mo.). Once obtained, the dNTPs may be placed into solution at working concentrations and stored according to the methods of the present invention.

ddNTPs

The ddNTP components of the present compositions serve as the "terminating agents" in the dideoxy nucleic acid sequencing methodologies, being incorporated into newly synthesized nucleic acids by the action of the polymerases. These ddNTPs—dideoxyadenosine triphosphate (ddATP), dideoxycytosine triphosphate (ddCTP), dideoxyguanosine triphosphate (ddGTP), dideoxythymidinetriphosphate (ddTTP), and for some applications dideoxyuridine triphosphate (ddUTP) and dideoxyinosine triphosphate (ddITP)—are available commercially from sources including Life Technologies, Inc. (Rockville, Md.), New England Biolabs (Beverly, Mass.) and Sigma Chemical Company (Saint Louis, Mo.). The ddNTPs may be unlabeled, or they may be detectably labeled by coupling them by methods known in the art with radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin) or other detection agents. Labeled ddNTPs may also be obtained commercially, for example from Life Technologies, Inc. (Rockville, Md.) or Sigma Chemical Company (Saint Louis, Mo.). Once obtained, the ddNTPs may be placed into solution at working concentrations and stored according to the methods of the present invention.

Buffers/Salts

All buffers and cofactor salts comprising the compositions of the present invention, and concentrated stock solutions thereof are available from a variety of commercial sources including Life Technologies, Inc. (Rockville, Md.) and Sigma Chemical Company (Saint Louis, Mo.). Particularly preferred buffers for use in forming the present compositions are the sulfate, hydrochloride, phosphate or free acid forms of tris-(hydroxymethyl)aminomethane (TRIS®), although alternative buffers of the same approximate ionic strength and pKa as TRIS® may be used with equivalent results. In addition to the buffer salts, cofactor salts such as those of potassium (preferably potassium chloride) and magnesium (preferably magnesium chloride or sulfate) are included in the compositions. Once obtained, the buffers and cofactor salts may be placed into solution at working concentrations and stored according to the methods of the present invention.

Detergents

At least one detergent may be included as a component of the present compositions, to provide for both increased stability and activity of the component enzymes. Nonionic detergents are preferred, to maintain a balanced ionic strength and prevent chelation of cofactors and aggregation or inactivation of proteins. Particularly preferred as detergents are TRITON X-100®, Brij 35, Tween 20 and Nonidet P-40 (NP-40), although other nonionic surfactants and mixtures thereof may also be used in the present compositions. These detergents are available commercially from sources such as Sigma Chemical Company (Saint Louis, Mo.), usually as concentrated aqueous solutions or in powder form. Once obtained, the detergents may be placed into solution at working concentrations and stored according to the methods of the present invention.

Antibodies

In additional embodiments of the invention, the compositions may optionally comprise one or more antibodies which specifically bind to the one or more thermostable enzymes, such as the one or more DNA polymerases, present in the compositions of the invention. According to this aspect of the invention, the one or more antibodies will specifically bind to the one or more thermostable enzymes (such as the one or more DNA polymerases) at temperatures below about 45° C.; as a result of this binding, the enzymatic activity of the enzyme will be completely or substantially completely inhibited. However, once the composition or reaction mixture containing the composition is raised to a temperature above about 60-65° C. (e.g., the temperatures at which standard PCR methods are conducted), the antibody is denatured and the activity of the enzyme is restored. Thus, such compositions will have utility in such applications as "Hot Start" PCR amplification protocols. Antibodies for use in this aspect of the invention include polyclonal antibodies, monoclonal antibodies, and enzyme-binding fragments (such as F(ab') or F(ab')$_2$ fragments) thereof.

According to the invention, any antibody or fragment thereof which specifically binds to one or more of the thermostable enzymes in the present compositions, such as the DNA polymerases, may be used, including but not limited to anti-Taq antibodies, anti-Tne antibodies, anti-Tma antibodies, anti-Pfu antibodies, anti-Pwo antibodies, anti-Tth antibodies, and the like. These and other antibodies suitable for use in this aspect of the invention may be obtained commercially, e.g., from Life Technologies, Inc. (Rockville, Md.). Alternatively, antibodies may be produced in animals by routine methods of production of polyclonal antibodies (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468-469 (1995) or monoclonal antibodies (see, e.g., Köhler et al., *Nature* 256:495 (1975); Köhler et al., *Eur. J. Immunol.* 6:511 (1976); Köhler et al., *Eur. J. Immunol.* 6:292 (1976); Hammerling et al., In: *Monoclonal Antibodies and T-Cell Hybridomas*, New York: Elsevier, pp. 563-681(1981); Kaufman, P. B., et al., In: *Handbook of Molecular and Cellular Methods in Biology and Medicine*, Boca Raton, Fla.: CRC Press, pp. 444-467 (1995)), using the corresponding thermostable enzyme (such as the corresponding DNA polymerase) as an immunogen.

Formulating the Reagent Compositions

Once the reagent components have been obtained, they are mixed at working concentrations to form a solution suitable for immediate use with or without dilution or addition of further reagents. The water used in the formulations of the present invention is preferably distilled, deionized and sterile filtered (through a 0.1-0.2 micrometer filter), and is free of contamination by DNase and RNase enzymes. Such water is available commercially, for example from Sigma Chemical Company (Saint Louis, Mo.), or may be made as needed according to methods well known to those skilled in the art.

Although the components of the present compositions may be admixed in any sequence, it is often preferable to first dissolve the buffer(s) and cofactor salts in water and to adjust the pH of the solution prior to addition of the remaining components. In this way, the pH-sensitive components (particularly the enzymes, ddNTPs and dNTPs) will be less subject to acid- or alkaline-hydrolysis during formulation.

To formulate the buffered salts solution, a buffer salt which is preferably a salt of tris(hydroxymethyl)aminomethane (TRIS®), and most preferably the hydrochloride salt thereof, is combined with a sufficient quantity of water to yield a solution having a TRIS® concentration of 5-150 millimolar, preferably 10-60 millimolar, and most preferably about 20-60 millimolar. To this solution, a salt of magnesium (preferably either the chloride or sulfate salt thereof) may be added to provide a working concentration thereof of 1-10 millimolar, preferably 1.5-5 millimolar, and most preferably about 1.5-2 millimolar. A salt of potassium (most preferably potassium chloride) may also be added to the solution, at a working concentration of 10-100 millimolar and most preferably about 50 millimolar. An ammonium salt, for example ammonium sulfate, may also be added to the mixture, at a working concentration of 2-50 millimolar, preferably 10-30 millimolar and most preferably 18 millimolar. Combinations of ammonium sulfate and potassium chloride (or other salts) may also be used in formulating the compositions of the present invention. A small amount of a salt of ethylenediaminetetraacetate (EDTA) may also be added (preferably about 0.1 millimolar), although inclusion of EDTA does not appear to be essential to the function or stability of the compositions of the present invention. After addition of all buffers and salts, this buffered salt solution is mixed well until all salts are dissolved, and the pH is adjusted using methods known in the art to a pH value of 7.4 to 9.2, preferably 8.0 to 9.0, and most preferably about 8.3 for compositions to be used in amplification or sequencing of nucleotide fragments up to about 5-6 kilobases in size (hereinafter referred to as "standard compositons"), and about 8.9 for compositions to be used for amplification or sequencing of nucleotide fragments larger than about 5-6 kilobases in size (hereinafter referred to as "large sequence compositions").

To the buffered salt solution, the remaining components of the present composition are added. It is well known in the field that the addition of one or more detergents to an aqueous buffer will aid in the subsequent solubilization of added proteins. Accordingly, at least one nonionic detergent such as TRITON X-100® (preferably at a working concentration of 0.1-1%), Brij 35 (preferably at a concentration of 0.01-1% and most preferably of about 0.1%) or Nonidet P-40 (NP-40, preferably as an admixture with a concentration of 0.004-1%, and most preferably in admixture with Tween 20 at a working concentration of 0.1% for standard compositions and 0.02% for large sequence compositions) may be added to the buffer solution. This detergent is preferably added prior to the introduction of the remaining components into the solution, although the detergent may equivalently be added at any step of formulation. Following formulation, the buffered salt solutions may be filtered through a low protein-binding filter unit that is available commercially (for example from Millipore Corporation, Bedford, Mass.) and stored until use.

The remaining components are then added to the solution to formulate the compositions of the present invention. At least one thermostable enzyme (e.g., DNA polymerase) is added and the solution is gently mixed (to minimize protein denaturation). For standard DNA amplification (including via PCR) or sequencing of DNA segments up to about 5-6 kilobases in length, any thermostable DNA polymerase (hereinafter the "primary polymerase") may be used in the standard compositions, although Taq, Tne, Tma, VENT™, DEEPVENT™, Pfu or Pwo polymerases are preferable at a working concentration in the solution of about 0.1-200 units per milliliter, about 0.1-50 units per milliliter, about 0.1-40 units per milliliter, about 0.1-36 units per milliliter, about 0.1-34 units per milliliter, about 0.1-32 units per milliliter, about 0.1-30 units per milliliter, or about 0.1-20 units per milliliter, and most preferably at a working concentration of about 20 units per milliliter. For amplification of DNA segments larger than 5-6 kilobases in length, large sequence compositions should be formulated by adding to the standard compositions a low concentration of one or more additional thermostable DNA polymerases (hereinafter the "secondary polymerase") containing a 3'-5' exonuclease activity. Particularly suited for this application are VENT™, Pfu, Pwo or Tne, and most preferably DEEPVENT™, DNA polymerases. The additional polymerase(s) should be added to the solution in sufficient quantity to give a final working concentration of about 0.0002-200 units per milliliter, about 0.002-100 units per milliliter, about 0.002-20 units per milliliter, about 0.002-2.0 units per milliliter, about 0.002-1.6 units per milliliter, about 0.002-0.8 units per milliliter, about 0.002-0.4 units per milliliter, or about 0.002-0.2 units per milliliter, most preferably at concentrations of about 0.40 units per milliliter.

It has heretofore been thought that the activity ratios of the primary to secondary polymerases should be maintaied at 4:1-2000:1 for large sequence amplification (see U.S. Pat. No. 5,436,149). It has now been discovered, however, that in the compositions of the present invention that activity ratios of the primary to secondary polymerases of 1:1, 1:2, 1:4, 1:5, 1:8, 1:10, 1:25, 1:50, 1:100, 1:250, 1:500, 1:1000 and 1:2000 may be suitable for amplification of large nucleotide sequences.

For nucleic acid sequencing, the reagent compositions may be used as formulated above. For nucleic acid sequencing by the dideoxy method (See U.S. Pat. Nos. 4,962,020, 5,173,411 and 5,498,523), however, preferably the mutant Tne DNA polymerase shown in SEQ ID NO:2 is added to the reagent compositions. Tne polymerase is added to the solution to give a working concentration of about 0.1-10,000 units per milliliter, about 0.1-5000 units per milliliter, about 0.1-2500 units per milliliter, about 0.1-2000 units per milliliter, about 0.1-1500 units per milliliter, about 0.1-1000 units per milliliter, about 0.1-500 units per milliliter, about 0.1-300 units per milliliter, about 0.1-200 units per milliliter, about 0.1-100 units per milliliter, or about 0.1-50 units per milliliter, and most preferably of about 300 units per milliliter.

For dideoxy sequencing, a solution of each ddNTP is also prepared. The base of each solution contains dATP, dCTP, dTTP, 7-deaza-GTP and/or other dNTPs, each at a working concentration of about 10-1000 micromolar, about 10-500 micromolar, about 10-250 micromolar, or about 10-100 micromolar, most preferably at a concentration of about 100 micromolar, in a solution of buffer and chelating salts, for example TRIS®-HCl most preferably at a working concentration of about 10 millimolar (pH about 7.5) and disodium-EDTA most preferably at a concentration of about 0.1 millimolar. To this base, one of the ddNTPs is added to make each of four solutions. Preferably, the sodium or lithium salt of ddATP, ddCTP, ddGTP or ddTTP is added to the solution to give a working concentration of the ddNTP of about 0.5-10 micromolar, about 0.5-8 micromolar, about 0.5-5 micromolar, about 0.5-3 micromolar, about 0.5-2.5 micromolar, or about 0.5-2 micromolar, and most preferably about 2 micromolar. For cycle sequencing applications, the pH of the ddNTP solutions will preferably be about 9.0, and the concentrations of ddNTPs may be lower, preferably about 0.05 to 1.0 micromolar or about 0.05 to 0.8 micromolar, and most preferably about 0.08 to 0.8 micromolar. For some applications, it may be desirable to also incorporate or substitute ddITP, ddUTP, and/or α-thio-dATP into the compositions at approximately the same working concentrations. Thus, four solutions are prepared, each containing one of the four ddNTPs, which are combined with the polymerase compositions of the present invention to carry out the four separate reactions used in dideoxy sequencing. Alternatively, for single-solution sequencing as disclosed in U.S. Pat. Nos. 4,962,020 and 5,173,411, the four ddNTPs may be combined into a single solution which is added to the polymerase compositions of the present invention to perform the sequencing reaction.

For nucleic acid amplification, including PCR, dNTP salts are added to the reagent compositions. Preferably, the sodium or lithium salts of dATP, dCTP, dGTP and dTTP are added to the solution to give a working concentration of each dNTP of 10-1000 micromolar, preferably 200-300 micromolar, and most preferably about 200 micromolar. For some applications, it may be desirable to also incorporate or substitute dITP or dUTP into the compositions at the same working concentrations.

In certain embodiments as noted above, one or more antibodies that specifically bind to the one or more thermostable enzymes in the compositions, such as the one or more DNA polymerases, may optionally be added to the compositions. Preferably, the antibodies are used in these compositions at an antibody to polymerase concentration ratio of up to about 100:1, up to about 50:1, up to about 25:1, up to about 20:1, up to about 15:1, up to about 10:1, up to about 9:1, up to about 8:1, up to about 7.5:1, up to about 7:1, up to about 6:1, up to about 5:1, up to about 4:1, up to about 3:1, up to about 2.5:1, up to about 2:1, or up to about 1:1. Most preferably, the antibodies are used in the compositions at an antibody to polymerase concentration ratio of about 1:1 to about 10:1, or about 1:1 to about 5:1.

To reduce component denaturation, storage of the reagent compositions is preferably in conditions of diminished light, e.g., in amber or otherwise opaque containers or in storage areas with controlled low lighting. The ready-to-use reagent compositions of the present invention are unexpectedly stable at ambient temperature (about 20°-25° C.) for about 4-10 weeks, are stable for at least one year upon storage at 4° C., and for at least two years upon storage at −20° C. Surprisingly, storage of the compositions at temperatures below freezing (e.g., −20° C. to −70° C.), as is traditional with stock solutions of bioactive components, is not necessary to maintain the stability of the compositions of the present invention.

In other preferred embodiments, the compositions of the present invention may be assembled into kits for use in nucleic acid amplification or sequencing. Sequencing kits according to the present invention comprise a carrier means, such as a box, carton, tube or the like, having in close confinement therein one or more container means, such as vials, tubes, ampules, bottles and the like, wherein a first container means contains a stable composition comprising a mixture of reagents, at working concentrations, which are at least one thermostable DNA polymerase, at least one buffer salt, at least one deoxynucleoside triphosphate, at least one dideoxynucleoside triphosphate, and optionally at least one antibody which specifically binds to at least one thermostable DNA polymerase present in the compositions. The sequencing kits may further comprise additional reagents and compounds necessary for carrying out standard nucleic sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing).

Similarly, amplification kits according to the present invention comprise carrier means, such as a box, carton, tube or the like, having in close confinement therein one or more container means, such as vials, tubes, ampules, bottles and the like, wherein a first container means contains a stable composition comprising a mixture of reagents, at working concentrations, which are at least one thermostable DNA polymerase, at least one buffer salt, at least one deoxynucleoside triphosphate, and optionally at least one antibody which binds specifically to at least one thermostable DNA polymerase present in the composition. The amplification kits encompassed by this aspect of the present invention may further comprise additional reagents and compounds necessary for carrying out standard nucleic amplification protocols (See U.S. Pat. Nos. 4,683,195 and 4,683,202, which are directed to methods of DNA amplification by PCR).

Use of the Reagent Compositions

The compositions and kits embodied in the present invention will have general utility in any application utilizing nucleic acid sequencing or amplification methodologies. Amplification methods in which the present compositions may be used include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Nucleic acid sequencing techniques which may employ the present compositions include dideoxy sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22):6531-6535, 1990), Arbitrarily Primed PCR (AP-PCR; Welsh, J., and McClelland, M., *Nucl. Acids Res.* 18(24):7213-7218, 1990), DNA Amplification Fingerprinting (DAF; Caetano-Anollés et al., *Bio/Technology* 9:553-557, 1991), microsatellite PCR or Directed Amplification of Minisatellite-region DNA (DAVID; Heath, D. D., et al., *Nucl. Acids Res.* 21(24): 5782-5785, 1993), and Amplification Fragment Length Polymorphism (AFLP) analysis (EP 0 534 858; Vos, P., et al., *Nucl. Acids Res.* 23(21):4407-4414, 1995; Lin, J. J., and Kuo, J., *FOCUS* 17(2):66-70, 1995). In particular, the compositions and kits of the present invention will be useful in the fields of medical therapeutics and diagnostics, forensics, and agricultural and other biological sciences, in any procedure utilizing thermostable DNA polymerases. Furthermore, the methods by which the compositions of the present invention are formulated may be extendable to all thermostable enzymes or mixtures thereof, and may allow the formulation of ready-to-use compositions of a variety of bioactive enzymes or other proteins that demonstrate increased stability upon extended storage at temperatures above freezing.

The compositions and kits of the invention are particularly useful in methods for amplifying and sequencing nucleic acid molecules. Nucleic acid amplification methods according to this aspect of the invention comprise contacting a nucleic acid molecule to be amplified with one or more of the compositions of the invention, thus providing a population of amplified copies of the nucleic acid molecule. Nucleic acid sequencing methods according to this aspect of the invention comprise contacting the nucleic acid molecule to be sequenced with one or more of the compositions of the invention. According to these methods, amplification and sequencing of the nucleic acid molecule may be accomplished by any of the above-described amplification and sequencing techniques, most preferably by PCR. The present amplification and sequencing methods are particularly useful for amplification and sequencing of large nucleic acid molecules (e.g., by "long PCR"), preferably nucleic acid molecules that are larger than about 4-8 kilobases in size, more preferably larger than about 5-7 kilobases in size, and most preferably nucleic acid molecules that are larger than about 7 kilobases in size.

It will be readily apparent to those of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Formulation of Standard Compositions

As an initial step in formulating stable, ready-to-use reagent compositions for nucleic acid amplification and sequencing, components were mixed in varying amounts as shown in Table 1 to provide 24 different formulations. The pH on all formulations was adjusted to about 8.3. After filtration through a low protein-binding filter, all compositions were formulated with 20 units/ml of Taq polymerase and were suitable for use as standard compositions for amplification or sequencing of nucleic acid fragments up to about 5-6 kilobases in size.

TABLE 1

FORMULATIONS OF STANDARD COMPOSITIONS

| | Formulation Number | | | | | | | |
|---|---|---|---|---|---|---|---|---|
| | 1 | 2 | 3 | 4 | 5 | 6 | 7 | 8 |
| Tris-HCl, pH 8.4 | 20 mM | 20 mM | 20 mM | 20 mM | 20 mM | 20 mM | 20 mM | 20 mM |
| KCl | 50 mM | 50 mM | 50 mM | 50 mM | 50 mM | 50 mM | 50 mM | 50 mM |
| $(NH_4)_2SO_4$ | 0 | 0 | 0 | 0 | 0 | 0 | 0 | 0 |
| dNTP | 200 µM | 200 µM | 200 µM | 200 µM | 200 µM Na | 200 µM Na | 200 µM Li | 200 µM Li |
| $MgCl_2$ | 1.5 mM | 1.5 mM | 1.5 mM | 1.5 mM | 1.5 mM | 1.5 mM | 1.5 mM | 1.5 mM |
| Detergents | 0.004% Tween20/NP40 | 0.1% Tween20/NP40 | 0.1% Tween20/NP40 | 0.1% Tween20/NP40 | 0.1% Tween20/NP40 | 0.004% Tween20/NP40 | 0.1% Tween20/NP40 | 0.004% Tween20/NP40 |
| Taq, U/ml | 20 | 20 | 20 | 20 | 20 | 20 | 20 | 20 |

TABLE 1-continued

FORMULATIONS OF STANDARD COMPOSITIONS

| | Formulation Number | | | | | | | |
|---|---|---|---|---|---|---|---|---|
| | 9 | 10 | 11 | 12 | 13 | 14 | 15 | 16 |
| Tris-HCl, pH 8.4 | 20 mM | 20 mM | 20 mM | 20 mM | 20 mM | 20 mM | 20 mM | 20 mM |
| KCl | 50 mM | 50 mM | 50 mM | 50 mM | 50 mM | 50 mM | 50 mM | 50 mM |
| $(NH_4)_2SO_4$ | 0 | 0 | 0 | 0 | 0 | 0 | 0 | 0 |
| dNTP | 200 μM | 200 μM | 200 μM | 200 μM | 200 μM | 200 μM | 200 μM | 200 μM |
| $MgCl_2$ | 1.5 mM | 3 mM | 3 mM | 3 mM | 3 mM | 3 mM | 3 mM | 3 mM |
| Detergents | 0.1% Tween20/NP40 | 0.1% Tween20/NP40 | 0.1% Brij35 | 0.1% TritonX-100 | 0.01% Tween20/NP40 | 0.01% Brij35 | 0.01% TritonX-100 | 1% Tween20/NP40 |
| Taq, U/ml | 20 | 20 | 20 | 20 | 20 | 20 | 20 | 20 |

| | Formulation Number | | | | | | | |
|---|---|---|---|---|---|---|---|---|
| | 17 | 18 | 19 | 20 | 21 | 22 | 23 | 24 |
| Tris-HCl, pH 8.4 | 20 mM | 20 mM | 20 mM | 20 mM | 20 mM | 20 mM | 50 mM (pH 9.0) | 20 mM (pH 8.8) |
| KCl | 50 mM | 50 mM | 50 mM | 50 mM | 50 mM | 50 mM | 0 | 10 mM |
| $(NH_4)_2SO_4$ | 0 | 0 | 0 | 0 | 0 | 0 | 20 mM | 10 mM |
| dNTP | 200 μM | 200 μM | 200 μM | 200 μM | 200 μM | 200 μM | 200 μM | 200 μM |
| $MgCl_2$ | 3 mM | 3 mM | 3 mM | 3 mM | 3 mM | 3 mM | 1.5 mM | 2 mM |
| Detergents | 1% Brij35 | 1% TritonX-100 | none | 0.1% Tween20/NP40 | 0.1% Tween20/NP40 | 0.1% Tween20/NP40 | 0.1% Tween20/NP40 | 0.1% TritonX100 |
| Taq, U/ml | 20 | 20 | 20 | 20 | 20 | 20 | 20 | 20 |

EXAMPLE 2

Stability of Standard Compositions

To examine the stability of the standard compositions formulated in Example 1, samples of each formulation were aliquoted and stored, under diminished light, at ambient temperature (about 20°-25° C.), 4° C., −20° C. and −70° C. Samples of each formulation from each temperature were taken daily for the first week, and weekly thereafter, and used in stability assays. These stability assays were performed by amplifying, via standard PCR, suboptimal amounts of human genomic DNA as a template using a template titration (if few samples were to be compared in a time point) or a fixed amount of template (if a larger number of samples were to be compared). To the desired amount of template DNA in a given formulation, 10 picomoles of primer was added, and the reaction mixtures were subjected to 35 cycles of PCR of 30 seconds at 94° C., 30 seconds at 55° C. and 1 minute/kilobase at 72° C. A portion of each reaction was then subjected to agarose gel electrophoresis and visualized by ethidium bromide fluorescence under ultraviolet illumination.

The results of these assays indicated that certain of the formulations demonstrated enhanced stability upon storage. As shown in FIG. 1, after about three months of storage at 4° C., formulations 15 and 19 had completely lost enzymatic activity, as evidenced by an absence of bands in the lanes corresponding to these samples. At this same time point, however, formulations 10-14, 16-18 and 20-24 demonstrated about the same levels of enzymatic activity as a freshly made ("control") formulation.

Figure 2:
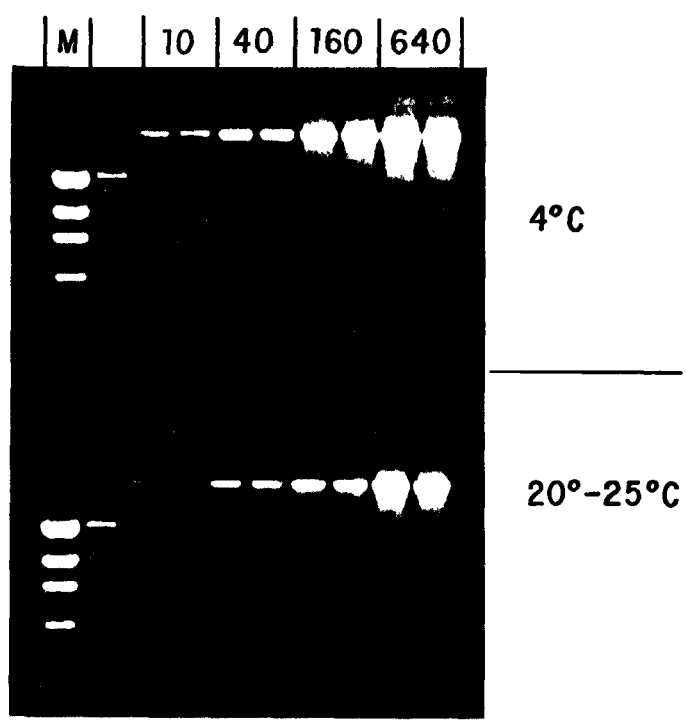
FIG. 2 is a photograph of an agarose gel (visualized by ethidium bromide fluorescence under ultraviolet illumination) of PCR amplification of a 4.1 kilobase human genomic DNA fragment using the amounts indicated (in nanograms) of template for each amplification reaction. The samples on the upper portion of the gel were amplified with a nucleic acid amplification composition stored for 10 weeks at 4° C., while those on the lower portion of the gel were amplified with a composition stored for 10 weeks at ambient temperature (about 20-25° C.). Leftmost lanes in each portion are markers as indicated in FIG. 1.

Storage temperature was also found to have a significant effect upon the stability of the formulations, even within a given formulation. As shown in FIG. 2, when samples of formulation 4 were examined after about 15 weeks of storage at either 4° C. or about 20-25° C., the samples stored at 4° C. retained full enzymatic activity when compared to a control sample. Those stored at about 20-25° C., however, had lost some activity, as indicated by the lower yields of the target fragment obtained at all template concentrations.

The results for all of the formulations at the various storage temperatures are summarized in Table 2.

TABLE 2

STABILITY OF STANDARD COMPOSITIONS

| Storage Temperature, °C. | Formulation Number[1] | | | | | | | |
|---|---|---|---|---|---|---|---|---|
| | 1 | 2 | 3 | 4 | 5 | 6 | 7 | 8 |
| 20-25 | <12 weeks | <12 weeks | <15 weeks | <12 weeks | nd[2] | nd | nd | nd |
| 4 | >26 weeks | >26 weeks | >56 weeks | >27 weeks | >8 weeks | >8 weeks | >8 weeks | >8 weeks |
| −20 | >13 weeks | >13 weeks | nd | >15 weeks | nd | nd | nd | nd |
| −70 | nd | nd | nd | >15 weeks | nd | nd | nd | nd |

| Storage Temperature, °C. | Formulation Number[1] | | | | | | | |
|---|---|---|---|---|---|---|---|---|
| | 9 | 10 | 11 | 12 | 13 | 14 | 15 | 16 |
| 20-25 | nd | <10 weeks | <6 weeks | <6 weeks | <12 weeks | <10 weeks | <7 days | <12 weeks |
| 4 | >40 weeks | >26 weeks | >26 weeks | >26 weeks | >26 weeks | >26 weeks | <1 day | >26 weeks |

TABLE 2-continued

STABILITY OF STANDARD COMPOSITIONS

| −20 | >10 weeks | >26 weeks | >26 weeks | >26 weeks | >26 weeks | >26 weeks | <7 days | >26 weeks |
| −70 | nd | nd | nd | nd | nd | nd | nd | nd |

| Storage Temperature, | Formulation Number[1] | | | | | | | |
|---|---|---|---|---|---|---|---|---|
| °C. | 17 | 18 | 19 | 20 | 21 | 22 | 23 | 24 |
| 20-25 | <6 weeks | <6 weeks | 0 days | <10 weeks | <10 weeks | <12 weeks | <6 weeks | <12 weeks |
| 4 | >26 weeks | >26 weeks | 0 days | >26 weeks | >26 weeks | >13 weeks | >26 weeks | >26 weeks |
| −20 | >26 weeks | >26 weeks | 0 days | >26 weeks | >26 weeks | >26 weeks | >26 weeks | >26 weeks |
| −70 | nd | nd | nd | nd | nd | nd | nd | nd |

[1]Formulation numbers correspond to those in Table 1;
[2]nd = not done.

These results indicate that several of the compositions unexpectedly maintained enzymatic activity for 6-12 weeks upon storage at 20-25° C., and for over one year at 4° C. Formulation 19, however, had completely lost activity within 24 hours of formulation. Formulation 15 also exhibited a rapid loss of activity.

For further analysis of the stability of these ready-to-use compositions, several formulations were stored at 20-25° C. or at 4° C. for up to six months, with samples taken monthly for stability assays performed by a determination of polymerase unit activity. The results of these assays are summarized in Tables 3 and 4.

TABLE 3

STABILITY OF STANDARD COMPOSITIONS
(PERCENTAGE OF ENZYME ACTIVITY REMAINING)
UPON STORAGE AT 20-25° C.

| Formulation No.[1] | 1 Month | 2 Months | 3 Months | 4 Months |
|---|---|---|---|---|
| 10 | 89 | 65 | nd[2] | nd |
| 11 | 106 | 3 | nd | nd |
| 12 | 106 | 91 | nd | nd |
| 13 | 93 | 72 | nd | nd |
| 14 | 91 | 76 | nd | nd |
| 15 | 78 | 63 | nd | nd |
| 16 | 94 | 85 | nd | nd |
| 17 | 89 | 90 | nd | nd |
| 18 | 90 | 84 | nd | nd |
| 19 | 0 | 0 | nd | nd |
| 20 | 88 | 81 | 72 | 77 |
| 21 | nd | 103 | nd | nd |
| 22 | 97 | 84 | nd | nd |
| 23 | 83 | 77 | nd | nd |
| 24 | 81 | 106 | nd | nd |

[1]Formulation numbers correspond to those in Table 1.
[2]nd = not done

TABLE 4

STABILITY OF STANDARD COMPOSITIONS
(PERCENTAGE OF ENZYME ACTIVITY REMAINING)
UPON STORAGE AT 4° C.

| Formulation No.[1] | 1 Month | 2 Months | 4 Months | 5 Months | 6 Months |
|---|---|---|---|---|---|
| 10 | 84 | 86 | 98 | nd[2] | 105 |
| 11 | 94 | 97 | 98 | nd | nd |
| 12 | 94 | 97 | 106 | nd | nd |
| 13 | 86 | 93 | 93 | nd | nd |
| 14 | 85 | 91 | 105 | nd | nd |
| 15 | 89 | 89 | 98 | nd | nd |
| 16 | 88 | 103 | 104 | nd | nd |
| 17 | 83 | 94 | 91 | nd | nd |
| 18 | 90 | 97 | 99 | nd | nd |
| 19 | 95 | 59 | nd | nd | 38 |
| 20 | 97 | 100 | 94 | 94 | 103 |
| 21 | 93 | 97 | 100 | nd | nd |
| 22 | 100 | 109 | 35 | nd | nd |
| 23 | 94 | 97 | 89 | nd | 107 |
| 24 | 93 | 94 | 97 | nd | nd |

[1]Formulation numbers correspond to those in Table 1.
[2]nd—not done

Several of the formulations were stable upon storage at 20-25° C., most notable formulation 20 which retained >70% of its enzymatic activity even after storage for four months at this temperature. As described earlier, formulation 19 had completely lost activity within the first month, as determined by the PCR assay. Interestingly, however, as determined by the polymerase unit activity assay, formulation 19 was stable for one month when stored at 4° C. but had lost substantial activity by the second month of storage at this temperature (Table 4). Formulation 20, shown previously to be stable upon extended storage at 20-25° C., was stable upon storage at 4° C. for at least six months.

Taken together, these results indicate that the compositions of the present invention are readily suitable for use in nucleic acid amplification reactions, and demonstrate extended stability upon storage at 20-25° C. or 4° C.

EXAMPLE 3

Formulation and Stability of Large Sequence Compositions

For use in amplification and sequencing of nucleic acid fragments larger than 5-6 kilobases, it has been suggested as described above that a mixture of Taq and VENT™ or DEEPVENT™ polymerases (U.S. Pat. No. 5,436,149; Barnes, Id.), or of Tth and either Tli, *Pyrococcus* or Tma (U.S. Pat. No. 5,512,462), be used. Accordingly, Taq and DEEPVENT™ DNA polymerases were formulated, at activity ratios of 100:1 (for samples 1-3) or 50:1 (for sample 4) into solutions containing the buffer salts, cofactors and detergents shown in Table 5. Each of these formulations was adjusted to about pH 9.1, which is optimal for the activity of DEEPVENT™ DNA polymerase (Bej and Mahbubani, Id). Samples were then stored at about 20-25° C. or at 4° C. and assayed weekly for 12 weeks, and monthly thereafter, in stability assays in which a 20 kilobase target in 100 nanograms of human genomic template was amplified by PCR. Reaction mixtures included 10 picomoles of primer and were subjected to 35 PCR cycles of 30 seconds at 94° C., 30 seconds at 62° C. and 1 minute/kilobase at 68° C. Portions of the reaction were subjected to agarose gel electrophoresis and were visualized by ethidium bromide fluorescence under ultraviolet illumination, as shown above for FIGS. 1 and 2. Results are summarized in Table 5.

TABLE 5

STABILITY OF LARGE SEQUENCE COMPOSITIONS

| Formulation No. | Formulation | Stability at: 20-25° C. | Stability at: 4° C. |
|---|---|---|---|
| 1 | 66 mM Tris-$SO_4$ (pH 9.1) 19.8 mM $(NH_4)_2$ $SO_4$ 2.2 mM $MgSO_4$ 22 units/ml Taq DNA Polymerase 0.22 units/ml DEEPVENT DNA Polymerase 0.11% Tween-20 0.011% NP-40 | <12 weeks | 11 months |
| 2 | 66 mM Tris-$SO_4$ (pH 9.1) 19.8 mM $(NH_4)_2$ $SO_4$ 2.2 mM $MgSO_4$ 24.42 units/ml Taq DNA Polymerase 0.242 units/ml DEEPVENT DNA Polymerase 0.066% Tween-20 0.066% NP-40 | <12 weeks | >11 months |
| 3 | 66 mM Tris-$SO_4$ (pH 9.1) 19.8 mM $(NH_4)_2$ $SO_4$ 2.2 mM $MgSO_4$ 22 units/ml Taq DNA Polymerase 0.22 units/ml DEEPVENT DNA Polymerase 0.01% Tween-20 0.01% NP-40 | nd[1] | 11 months |
| 4 | 66 mM Tris-$SO_4$ (pH 9.1) 19.8 mM $(NH_4)_2$ $SO_4$ 2.2 mM $MgSO_4$ 22 units/ml Taq DNA Polymerase 0.44 units/ml DEEPVENT DNA Polymerase 0.01% Tween-20 0.01% NP-40 | nd[1] | 11 months |

[1]nd = not done

Upon storage at ambient temperature (20°-25° C.), all of the formulations were stable for 6-12 weeks. Storage of these formulations at 4° C. provided enhanced stability of over 11 months. Similar results may be obtained with formulations in which Taq and Tne DNA polymerases were used in an activity ratio of 1:1, 1:2, 1:4, 1:5, 1:8, 1:10, 1:25, 1:50, 1:100, 1:250, 1:500, 1:1000 or 1:2000. These results indicate that the large sequence compositions of the present invention are readily suitable for use in amplification of nucleic acid sequences larger than 5-6 kilobases and demonstrate extended stability upon storage at 20° to 25° C., or at 4° C.

EXAMPLE 4

Combinations of *Thermus flavis* (Tfl) DNA Polymerase and *Thermotoga neapolitana* (Tne) DNA Polymerase To examine other DNA polymerase compositions for their utility in amplification of nucleic acid molecules, a mixture of Tfl and Tne DNA polymerases, at a 1:1 ratio, was used to amplify the 2.7 kilobase Puc19 plasmid. Amplification reactions were in a 50 µl final volume in buffer containing 1 mM magnesium acetate. 80 pg of Puc19 linearized by treatment with AdtII was used as the template, and was contacted with 1 µl of enzyme mixture. PCR conditions were 1 min at 94° C., followed by 35 cycles of 94° C. for 30 seconds/60° C. for 30 seconds/68° C. for 5 minutes.

Upon analysis of the amplification products by gel electrophoresis, this composition comprising Tfl and Tne oDNA polymerases was found to efficiently amplify the 2.7 kilobase Puc19 plasmid. The efficiency of amplification was comparable to amplification of Puc19 using 1 µl of Taq DNA polymerase.

EXAMPLE 5

Amplification of Genomic DNA Using Tfl/Tne Compositions

Having demonstrated that compositions comprising Tfl and Tne DNA polymerases efficiently amplify plasmid-sized nucleic acid molecules, these compositions were examined for their ability to amplify nucleic acid molecules from genomic DNA templates. Six different primer sets were constructed (ranging in size from 0.25 to 4.1 kilobases) and used to amplify the human β-globin gene from a genomic DNA template from the K562 human leukemia cell line. Each reaction was performed in a volume of 50 µl comprising template at 40 ng/reaction, and Tfl/Tne mixture at either 0.5 unit/reaction or 1 unit/reaction (Tfl and Tne at a 1:1 ratio in both mixtures). PCR conditions were 1 min at 94° C., followed by 35 cycles of 94° C. for 30 seconds/55° C. for 30 second/68° C. for 5 minutes.

Upon analysis of the amplification products by gel electrophoresis, efficient amplification was observed for all primers. The sizes of the amplification products produced using the different primers were 0.25 kilobase, 0.7 kilobase, 1.1 kilobases, 2.0 kilobases and 4.1 kilobases. These results demonstrate that the Tfl/Tne compositions efficiently amplify nucleic acid molecules derived from genomic DNA templates.

EXAMPLE 6

Use of Various Enzyme Ratios in DNA Polymerase Compositions

To determine the efficacy of different enzyme ratios in nucleic acid amplification, a composition comprising a higher amount of Tne (3' exo+) DNA polymerase than Tfl (3' exo−) DNA polymerase was made and tested for its ability to amplify Puc19 and the β-globin gene. A 1:3 mixture of Tfl/Tne was made and used to amplify Puc19 under the conditions described in Example 4, and β-globin under the conditions described in Example 5.

Upon analysis of the amplification products by gel electrophoresis, efficient amplification was observed for both Puc19 and for β-globin (all template sizes). These results demonstrate that compositions in which a 3' exo+ DNA polymerase (Tne) is present in higher quantity than a 3' exo− DNA polymerase (Tfl) efficiently amplify nucleic acid molecules derived from plasmid and genomic DNA templates.

EXAMPLE 7

Amplification of Large Nucleic Acid Molecules Using DNA Polymerase Mixtures

Having demonstrated that compositions comprising mixtures of 3' exo+ and 3' exo− DNA polymerases efficiently amplify plasmid-sized and small genomic nucleic acid molecules, such compositions were examined for their ability to amplify larger nucleic acid molecules. For these studies, mixtures of Taq (3' exo+) DNA polymerase and Tma (3' exo−) DNA polymerase (ULTma™; LTI, Rockville, Md.) were prepared. Two sets of mixtures were prepared: one set contained 1 unit of Taq and varying amounts of ULTma (0.3 unit, 0.6 unit, 0.8 unit or 1 unit), and the other set contained no Taq and only varying amounts of ULTma (0.3 unit, 0.6 unit, 0.8 unit or 1 unit). These compositions were used to amplify 80 mg of human genomic DNA using primers specific for a 7.5 kilobase region of the human β-globin gene. PCR conditions were 1 min at 94° C., followed by 35 cycles of 94° C. for 30 seconds/60° C. for 30 seconds/68° C. for 5 minutes.

Upon analysis of the amplification products by gel electrophoresis, the 7.5 kilobase β-globin fragment was found to be efficiently amplified by all compositions comprising both Taq and Tma DNA polymerase. Compositions comprising only Tma DNA polymerase, however, were unable to amplify this large fragment. In control experiments, compositions comprising only Taq DNA polymerase were also unable to amplify this large fragment. These results demonstrate that compositions comprising a mixture of 3' exo+ and 3' exo− DNA polymerases are useful in efficiently amplifying large nucleic acid molecules, particularly in amplifying nucleic acid molecules larger than about 7 kilobases in size.

EXAMPLE 8

Amplification of Large Nucleic Acid Molecules Using Various Ratios of Taq and Tma DNA Polymerases Having demonstrated that compositions comprising mixtures of 3' exo+ (Taq) and 3' exo− (Tma) DNA polymerases efficiently amplify large nucleic acid molecules, compositions comprising these enzymes in various ratios were made and tested for their abilities to amplify the 7.5 kilobase β-globin gene fragment from Example 7. Two sets of mixtures were prepared: one set contained 1 unit of ULTma DNA polymerase and different amounts (0.25, 0.5, 0.6, 0.7, 0.8, 0.9 or 1.0 unit) of Taq DNA polymerase, and the other set contained 1 unit of Taq DNA polymerase and different amounts (1.0, 1.1, 1.2, 1.3, 1.4, 1.5, 2.0, 3.0, 4.0 or 6.0 units) of ULTma DNA polymerase. Amplification templates, primers and cycling conditions were as described for Example 7.

Upon analysis of the amplification products by gel electrophoresis, efficient amplification of the 7.5 kilobase β-globin gene was observed for the first set of JO mixtures only in those compositions containing 0.5 to 1.0 unit of Taq DNA polymerase and 1.0 unit of ULTma. Compositions in this set containing less than 0.5 unit of Taq DNA polymerase did not amplify this fragment. However, all enzyme mixtures in the other set, i.e., compositions comprising 1.0 unit of Taq DNA polymerase and 1.0 to 6.0 units of ULTma DNA polymerase, demonstrated efficient amplification of the 7.5 kilobase fragment. In separate experiments, a 13.5 kilobase fragment of the β-globin gene was efficiently amplified using mixtures containing a 1:1 or a 1:2 ratio of Taq to ULTma. Together, these results indicate that compositions in which Tina DNA polymerase is present in equal or higher quantity than Taq DNA polymerase efficiently amplify large nucleic acid molecules, particularly those that are larger than about 7-13 kilobases in size.

EXAMPLE 9

Use of Taq and Tne DNA Polymerase Mixtures for Long PCR

To determine if other DNA polymerases could be used in compositions also comprising Taq DNA polymerase in amplification of large nucleic acid molecules, various mixtures of Taq and Tne DNA polymerases were made. For these experiments, a Tne DNA polymerase deletion mutant (5' exo−; 3' exo+) was mixed in amounts ranging from 0.05 to 2.0 units with 1 unit of Taq DNA polymerase and used to amplify the 7.5 kilobase β-globin fragment under conditions described for Example 7.

Upon analysis of the amplification products by gel electrophoresis, all of the combinations of Tne and Taq DNA polymerases were found to efficiently amplify the 7.5 kilobase DNA fragment. These results indicate that compositions comprising combinations of Taq and Tne DNA polymerases are useful in amplifying large nucleic acid molecules, particularly those larger than about 7 kilobases in size.

EXAMPLE 10

Preparation and Use of Compositions Comprising Anti-Taq Antibodies

To examine the stability of ready-to-use PCR reagents containing anti-Taq antibodies, Taq DNA polymerase was reacted with monoclonal antibody TP4-3 at ratios of 5:1, 2:1, 1:1 and 0:1 of antibody to Taq DNA polymerase. Binding of the antibody to Taq DNA polymerase inhibited polymerase activity of Taq almost completely at 5:1 and 2:1 ratios. The 1:1 ratio of antibody to Taq resulted in partial inhibition of polymerase activity ranging from 54% to 83% of the control Taq DNA polymerase with no antibody.

The ready-to-use reaction mixtures were stored at 4° C. or −20° C. for determination of stability of Taq DNA polymerase as well as stability of anti-Taq antibodies. Long-term storage of these mixtures showed no reduction in activity of Taq DNA polymerase or anti-Taq antibody after 17 months at 4° C. or −20° C. (Table 6).

TABLE 6

Stability of Ready-to-Use PCR Reagents

| Antibody:Taq Ratio | Control Fresh Mixtures Antibody Activity[1] | | | | Ready-to-Use Reagents (4° C. Storage) Antibody Activity | | Ready-to-Use Reagents (−20° C Storage) Antibody Activity | |
|---|---|---|---|---|---|---|---|---|
| | A | B | C | D | 14 months | 17 months | 14 months | 17 months |
| 5:1 | 97% | 98% | 97% | 97.9% | 94.8% | 97.5% | 94.8% | 98.5% |
| 2:1 | N.D.[2] | 96.9% | 96.4% | N.D. | N.D. | N.D. | 94.8% | 98% |
| 1:1 | 54% | 79% | 82.6% | 68% | 71% | 65% | 73% | 67% |
| 0:1 (control) | 0% | 0% | 0% | 0% | 0% | 0% | 0% | 0% |

[1]Antibody activity is expressed as % inhibition of DNA polymerization activity compared to no antibody (0:1 ratio) control.
[2]N.D. = not determined.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of amplifying a nucleic acid molecule comprising:
storing a composition at about 20° C. to 25° C. for at least one day, said composition lacking said nucleic acid molecule and comprising a mixture of reagents, said mixture of reagents comprising
a) at least one DNA polymerase;
b) at least one buffer salt; and
c) at least one dNTP;
wherein said DNA polymerase in said composition retains at least 70% of its enzyme activity after storage of said composition at about 20° C. to 25° C. for one day;
contacting said nucleic acid molecule with said stored composition under conditions sufficient to amplify said nucleic acid molecule; and
amplifying said nucleic acid molecule.

2. The method of claim 1, wherein said DNA polymerase retains at least 70% of its enzyme activity after storage of said composition at about 20° C. to 25° C. for one week.

3. The method of claim 1, wherein said DNA polymerase retains at least 70% of its enzyme activity after storage of said composition at about 20° C. to 25° C. for two weeks.

4. The method of claim 1, wherein said DNA polymerase retains at least 70% of its enzyme activity after storage of said composition at about 20° C. to 25° C. for four weeks.

5. The method of claim 1, wherein said DNA polymerase retains at least 90% of its enzyme activity after storage of said composition at about 20° C. to 25° C. for one week.

6. The method of claim 1, wherein said DNA polymerase retains at least 90% of its enzyme activity after storage of said composition at about 20° C. to 25° C. for two weeks.

7. The method of claim 1, wherein said DNA polymerase is a thermostable DNA polymerase.

8. The method of claim 1, wherein said DNA polymerase is selected from a Taq DNA polymerase, a Tne DNA polymerase, a Tma DNA polymerase, a Pfu DNA polymerase, a Pwo DNA polymerase, VENT™ DNA polymerase, DEEPVENT™ DNA polymerase, and mutants thereof.

9. The method of claim 1, wherein said DNA polymerase is Taq DNA polymerase.

10. The method of claim 1, wherein said amplifying is accomplished by PCR.

11. The method of claim 1, wherein said composition further comprises a magnesium salt.

12. The method of claim 1, wherein said at least one dNTP comprises one or more of dATP, dTTP, dGTP, dCTP and dUTP.

13. The method of claim 1, wherein said composition further comprises a detergent.

14. The method of claim 13, wherein said detergent is a non-ionic detergent.

15. The method of claim 13, wherein said detergent is selected from the group consisting of Triton X-100, Nonidet P-40, Tween 20 and Brij 35.

16. The method of claim 13, wherein said detergent is at a concentration of about 0.004% to about 1% in said composition.

17. A method for amplifying a nucleic acid molecule comprising:
contacting said nucleic acid molecule with a composition previously stored at about 20° C. to 25° C. for at least one day to form a reaction mixture;
incubating said reaction mixture under conditions sufficient to amplify said nucleic acid molecule; and
amplifying said nucleic acid molecule;
said stored composition lacking said nucleic acid molecule and comprising a mixture of reagents, said mixture of reagents comprising
a) at least one DNA polymerase;
b) at least one buffer salt; and
c) at least one dNTP;
wherein said DNA polymerase in said composition retains at least 70% of its enzyme activity after storage of said composition at about 20° C. to 25° C. for one day.

18. The method of claim 17, wherein said composition further comprises a magnesium salt.

19. The method of claim 17, wherein said at least one dNTP comprises one or more of dATP, dTTP, dGTP, dCTP and dUTP.

20. The method of claim 17, wherein said DNA polymerase is selected from a Taq DNA polymerase, a Tne DNA polymerase, a Tma DNA polymerase, a Pfu DNA polymerase, a Pwo DNA polymerase, VENT™ DNA polymerase, DEEPVENT™ DNA polymerase, and mutants thereof.

21. The method of claim 17, wherein said amplifying is accomplished by PCR.

22. The method of claim 17, wherein said composition further comprises a detergent.

23. The method of claim 22, wherein said detergent is a non-ionic detergent.

24. The method of claim 22, wherein said detergent is selected from the group consisting of Triton X-100, Nonidet P-40, Tween 20 and Brij 35.

25. The method of claim 22, wherein said detergent is at a concentration of about 0.004% to about 1% in said composition.

* * * * *